US012280051B2

United States Patent
Ramos Vernieri et al.

(10) Patent No.: US 12,280,051 B2
(45) Date of Patent: Apr. 22, 2025

(54) PHARMACEUTICAL COMPOSITION FOR TOPICAL WOUND TREATMENT

(71) Applicants: CONSEJO NACIONAL DE INVESTIGACIONES CIENTIFICAS Y TECNICAS, Buenos Aires (AR); UNIVERSIDAD NACIONAL DE TUCUMAN, Provincia de Tucuman (AR); UNTECH INC., Lewes, DE (US)

(72) Inventors: Alberto Ramos Vernieri, San Miguel de Tucumán (AR); Maria De Los Angeles Lazarte, San Miguel de Tucumán (AR); Romina Mabel Chavez Jara, San Miguel de Tucumán (AR); Nicolas Abel Cerusico, San Miguel de Tucumán (AR)

(73) Assignees: CONSEJO NACIONAL DE INVESTIGACIONES CIENTIFICAS Y TECNICAS, Buenos Aires (AR); UNIVERSIDAD NACIONAL DE TUCUMAN, Provincia de Tucuman (AR); UNTECH INC., Lewes, DE (US)

( * ) Notice: Subject to any disclaimer, the term of this patent is extended or adjusted under 35 U.S.C. 154(b) by 315 days.

(21) Appl. No.: 17/713,746

(22) Filed: Apr. 5, 2022

(65) Prior Publication Data

US 2022/0226325 A1    Jul. 21, 2022

Related U.S. Application Data

(63) Continuation of application No. 17/323,752, filed on May 18, 2021, now Pat. No. 11,382,913.

(51) Int. Cl.
*A61K 31/515* (2006.01)
*A61K 31/085* (2006.01)
(Continued)

(52) U.S. Cl.
CPC .......... *A61K 31/515* (2013.01); *A61K 31/085* (2013.01); *A61K 31/19* (2013.01);
(Continued)

(58) Field of Classification Search
CPC .... A61K 31/085; A61K 31/19; A61K 31/375; A61K 31/515; A61K 31/717; A61K 47/26; A61K 9/0014; C12N 9/22
See application file for complete search history.

(56) References Cited

U.S. PATENT DOCUMENTS

2007/0292195 A1    12/2007  May et al.
2009/0022779 A1    1/2009   Kelly et al.
(Continued)

FOREIGN PATENT DOCUMENTS

WO    2006/006167 A1    1/2006
WO    2018/218242 A1    11/2018

OTHER PUBLICATIONS

Kyaw, B.M., et al., "Need for Improved Definition of Chronic Wounds in Clinical Studies", Acta dermato-venereologica, 98 (1-2), 157-158, 2018.
(Continued)

*Primary Examiner* — Savitha M Rao
(74) *Attorney, Agent, or Firm* — Norris McLaughlin, P.A.

(57) ABSTRACT

A pharmaceutical composition for topical wound treatment comprising one or more nitrogenous heterocyclic compound of 5 or 6 atoms with imide group; one or more deoxyribonuclease enzyme with activity pH between 4.5 and 6.5; and one or more carboxylic acid; kits and process to obtain this pharmaceutical composition and uses for wounds treatment.

14 Claims, 11 Drawing Sheets

(51) Int. Cl.

| | |
|---|---|
| *A61K 31/19* | (2006.01) |
| *A61K 31/375* | (2006.01) |
| *A61K 31/717* | (2006.01) |
| *A61K 47/26* | (2006.01) |
| *C12N 9/22* | (2006.01) |

(52) U.S. Cl.
CPC .......... *A61K 31/375* (2013.01); *A61K 31/717* (2013.01); *A61K 47/26* (2013.01); *C12N 9/22* (2013.01)

(56) References Cited

U.S. PATENT DOCUMENTS

| | | |
|---|---|---|
| 2010/0266689 A1 | 10/2010 | Simonton et al. |
| 2011/0086101 A1 | 4/2011 | Madhyastha et al. |
| 2012/0039838 A1 | 2/2012 | Zhang et al. |
| 2016/0243164 A1 | 8/2016 | Yates et al. |

OTHER PUBLICATIONS

Martinengo, L., et al.: "Prevalence of chronic wounds in the general population: systematic review and meta-analysis of observational studies", Annals of epidemiology, 29, 8-15, 2019.
Olsson, M., et al.: "The humanistic and economic burden of chronic wounds: a systematic review", Wound Repair and Regeneration, 27(1), 114-125, 2019.
Zhao, R., et al.: "Inflammation in chronic wounds", International journal of molecular sciences, 17(12), 2085, 2016.
Morton, L.M., et al.: "Wound healing and treating wounds: Differential diagnosis and evaluation of chronic wounds", Journal of the American Academy of Dermatology, 74(4), 589-605, 2016.
Rezvani Ghomi, E., et al.: "Wound dressings: Current advances and future directions", Journal of Applied Polymer Science, 136 (27), 47738, 2019.
Snyder, D., et al.: "Skin substitutes for treating chronic wounds", https://www.ncbi.nlm.nih.gov/books/NBK554220/?report=printable, 2020.
El-Sabbagh, A.H.,: "Negative pressure wound therapy: an update", Chinese Journal of Traumatology, 20 (2), 103-107, 2017.
Parei, F., et al.: "Role of growth factors and biomaterials in wound healing", Artificial cells, nanomedicine, and biotechnology, 46 (sup1), 906-911, 2018.
Jones, M.W., et al.: "Hyperbaric Therapy For Wound Healing", https://europepmc.org/article/NBK/nbk459172, 2017.
Jones, R.E., et al.: "Management of chronic wounds—2018", Jama, 320 (14), 1481-1482, 2018.
Warriner, R., et al.: "Infection and the chronic wound: a focus on silver", Adv Skin Wound Care; 18 (Suppl 1): 2-12, 2005.
Miller, A.C., et al.: "Silver sulfadiazine for the treatment of partial-thickness burns and venous stasis ulcers", J Am Acad Dermatol; 66(5): e159-65, 2012.
Skog, E. et al.: "A randomized trial comparing cadexomer iodine and standard treatment in the out-patient management of chronic venous ulcers", Br J Dermatol; 109(1): 77-83, 1983.
Mober, S., et al.: "A randomized trial of cadexomer iodine in decubitus ulcers", J Am Geriatr Soc; 31(8): 462-5, 1983.
Lipsky, B.A., et al.: "Topical antimicrobial therapy for treating chronic wounds", Clin Infect Dis; 49(10):1541-1549, 2009.
Draelos, Z.D., et al.: "A comparison of postprocedural wound care treatments: do antibiotic-based ointments improve outcomes", J Am Acad Dermatol; 64(3 Suppl): S23-29, 2011.
Taylor, S.C., et al.: "Postprocedural wound-healing efficacy following removal of dermatosis papulosa nigra lesions in an African American population: a comparison of a skin protectant ointment and a topical antibiotic", J Am Acad Dermatol; 64(3 Suppl): S30-35, 2011.
Liu, W.L., et al.: "Combined debridement in chronic wounds: A literature review", Chinese Nursing Research, 4(1), 5-8, 2017.
Han, G, et al.: "Chronic wound healing: a review of current management and treatments", Advances in therapy, 34(3), 599-610, 2017.
Barnett, S.E., et al.: "The effects of calcium alginate on wound healing", Ann R Coll Surg Engl., 1987; 69(4):153-155.
Cullen, B., et al.: "Mechanism of action of Promogran, a protease modulating matrix, for the treatment of diabetic foot ulcers", Wound Repair Regen, 10(1): 16-25, 2002.
Valdez, J., et al.: "Probiotics and their potential use in wound treatment", Probiotics: Immunobiotics and Immunogenics, 298-335, 2013 (book).
Ramos, A.N., et al.: "Compounds from Lactobacillus plantarum culture supernatants with potential pro-healing and anti-pathogenic properties in skin chronic wounds", Pharmaceutical biology, 53(3), 350-358, 2015.
Lindon, S., et al.: "Biotechnological design to optimize the production of bioactive Lactobacillus plantarum by-products: novel chronic wound treatment", vol. 7, Issue 7, 2762-2774, 2016.
Nagoak, T., et al.: "Delayed wound healing in the absence of intercellular adhesion molecule-1 or L-selectin expression", The American journal of pathology, 157(1), 237-247, 2000.
Xu, Z., et al.: "Advances and impact of antioxidant hydrogel in chronic wound healing", Advanced Healthcare Materials, 9(5), 1901502, 1-11, 2020.
Fitzmaurice, S.D., et al.: "Antioxidant therapies for wound healing: a clinical guide to currently commercially available products", Skin pharmacology and physiology, 24(3), 113-126, 2011.
Cano Sanchez, M., et al.: "Targeting oxidative stress and mitochondrial dysfunction in the treatment of impaired wound healing: a systematic review", Antioxidants, 7(8), 98, 2018.
Bikker, A., et al.: "Ascorbic acid deficiency impairs wound healing in surgical patients: Four case reports", International Journal of Surgery Open, 2016.
Houwing, R., et al.: "An unexpected detrimental effect on the incidence of heel pressure ulcers after local 5% DMSO cream application: A randomized, double-blind study in patients at risk for pressure ulcers", Wounds; 20: 84-88, 2008.
Li, Y., et al.: "New developments and novel therapeutic perspectives for vitamin C", The Journal of nutrition, 137(10), 2171-2184, 2007.
Ajwee, D.M., et al.: "Ethosuximide and phenobarbital promote wound healing via enhancing collagenization", Chemical Biology & Drug Design, 79(1), 137-142, 2012.
Goldberg, S. R., et al.: "What Makes Wounds Chronic", Surgical Clinics, 100(4), 681-693, 2020.
Snyder, R.J., et al.: "Components and quality measures of DIME (Devitalized Tissue, Infection/Inflammation, Moisture Balance, and Edge Preparation) in wound care", Adv Skin Wound Care; 29(5): 205-215, 2016.
Darwin, E., et al.: "Healing chronic wounds: current challenges and potential solutions", Current dermatology reports, 7(4), 296-302, 2018.
Malone, M., et al.; "The prevalence of biofilms in chronic wounds: a systematic review and meta-analysis of published data", Journal of Wound Care, 26(1), 20-25, 2017.
Ammons M.C.; "Anti-biofilm strategies and the need for innovations in wound care", Recent patents on anti-infective drug discovery, 5(1), 10-17, 2010.
Brown, A.; "Managing exudate and maceration in venous leg ulceration within the acute health setting", British Journal of Nursing, 26 (Sup20), S18-S24, 2017.
Tardaguila, G. A., et al. (2019). Metalloproteinases in chronic and acute wounds: A systematic review and meta-analysis. Wound Repair and Regeneration, 27(4), 415-420.
Paschou, S.A., et al.; "Pain management of chronic wounds: Diabetic ulcers and beyond", Maturitas, 117, 17-21, 2018.
Sharma, O.P., et al.; "DPPH antioxidant assay revisited", Food chemistry, 113(4), 1202-1205, 2009.
Bennett, N.T., et al.: "Growth-Factors and Wound-Healing", Role in Normal and Chronic Wound-Healing, Am J Surg; 166: 74-81, (Jun. 1993.
Raffetto, J.D .: "Pathophysiology of wound healing and alterations in venous leg ulcers-review"; Phlebology; 31:56-62, 2016.

(56) References Cited

OTHER PUBLICATIONS

Han, G., et al.: "Chronic Wound Healing: A Review of Current Management and Treatments", Adv Ther ;34(3): 599-610, 2017.
Johnson, K. E., et al.: "Vascular Endothelial Growth Factor and Angiogenesis in the Regulation of Cutaneous Wound Repair", Adv Wound Care; 3(10): 647-661, 2014.
Kearns, M. T., et al.: "Vascular endothelial growth factor enhances macrophage clearance of apoptotic cells", Am J Physiol—Lung Cell Mol Physiol; 302(7): 711-718, 2012.
Seeger, M. A., et al.: "The Roles of Growth Factors in Keratinocyte Migration", Adv Wound Care; 4(4): 213-224, 2015.
Dunn, L., et al.: "Murine model of wound healing", JoVE (Journal of Visualized Experiments), (75), e50265, 2013.
Galiano, R.D., et al.: "Quantitative and reproducible murine model of excisional wound healing", Wound repair and regeneration, 12(4), 485-492, 2004.
Notification Concerning Transmittal of International Preliminary Report on Patentability for corresponding application PCT/US2020/049318 dated Mar. 17, 2022.
International Preliminary Report on Patentability with Written Opinion of International Searching Authority for corresponding application PCT/US2020/049318 dated Nov. 30, 2020.
Lazarus R. A. et al., "Recombinant Human Deoxyribonuclease I", Pharmaceutical Biotechnology, Springer, Chatn., Apr. 14, 2019 (Apr. 4, 2019), pp. 471-488, retrieved from the Internet: < DOI: 10.1007/978-3-030-00710-2_22 >.

PHARMACEUTICAL COMPOSITION FOR TOPICAL WOUND TREATMENT

CROSS-REFERENCE TO RELATED APPLICATIONS

This application is a continuation of U.S. patent application Ser. No. 17/323,752, filed on May 18, 2021, which is a continuation of International Patent Application No. PCT/US20/49318, filed Sep. 4, 2020, which claims the benefit of priority to U.S. Provisional Application No. 62/896,784, filed Sep. 6, 2019, the disclosures of each of which being incorporated herein by reference in their entirety

FIELD OF THE INVENTION

The present invention relates to topical pharmaceutical compositions for the treatment of wounds. Furthermore, it also relates to the field of topical pharmaceutical compositions and formulations useful for the treatment of chronic wounds.

STATE OF ART

Chronic wounds, understood as those that do not heal in a series of ordered stages and in predictable times, such as venous ulcers, diabetic foot ulcers, bedsores, pressure ulcers, ischemic ulcers, atypical lesions, among others, are injuries that do not heal (1). They affect about 2% of the world population (2) and represent a big economic problem for health systems (3). Chronic wounds are detained in a chronic inflammatory state that avoids healing (4), although the failure in healing is multifactorial (5). Chronic wounds were studied profusely by scientists resulting in a large number of products trying to provide a therapeutic solution. However, to date there is no holistic and effective treatment for these types of wounds.

There is a multiplicity of products for chronic wounds in the market. Physicians usually use a combination of therapies for wound infection, wound debridement and wound care (6). These kinds of products do not ensure healing and doctors must often recur to use also skin substitutes (7), vacuum assisted closure (8), growth factors (9) and hyperbaric therapy (10). However, none of them can offer all therapeutic requirements at the same time and therefore they also show a limited therapeutic efficacy (11).

Among the products that could be mentioned for wound infection: 1) Silver has a broad spectrum of activity and is available in numerous forms. However, it is necessary for a sustained release of silver in high enough concentrations to retain efficacy. For example, to work properly silver nitrate has to be administered 12 times a day (12). Furthermore, a recent review found no convincing evidence that silver sulfadiazine has any effect on wound healing overall, despite its common use among practitioners (13). 2) Iodine-containing compounds (i.e cadexomer iodine—iodine within a starch lattice formed into microbeads) have long been used in wound healing but there have been some concerns with toxicity of iodine-containing compounds, especially over large wound areas (14, 15). 3) Topical formulations of antibiotics have also been developed to apply to wound sites. However, recent studies with routine administration of antibiotic ointment lead to no better outcomes but often resulting in patient discomfort, along with the possibility of antibiotic resistance and contact dermatitis (16-18).

The vast majority of pathogens in chronic wounds are able to adhere together into biofilms, which represent tightly packed masses surrounding a polymeric matrix, thus helping to evade destruction by antibiotics and immune systems. This creates not only a physical barrier to wound healing but one in which the normal resolution of the inflammatory phase may be prolonged and addressing biofilms has become a major challenge in wound healing. However, there are no anti-biofilm products with a bacterial broad spectrum for chronic wounds. In fact, to be effective in chronic wounds, a product may offer bacteriostatic, bactericide, biofilm inhibition and biofilm disruption properties at the same time.

Wound debridement (19) involves the removal of non-viable tissue material to expose healthy, well-perfused tissue that is able to proliferate and populate the wound bed via epithelial cell migration, rather than keeping necrotic debris which only serves as fuel for infection and impedes wound healing. Surgical debridement is an important component of wound care, but it has all the inconveniences that surgical procedures have, like infections, pain, costs and patient discomfort. Autolytic debridement refers to the self-activation of endogenous enzymes involved in fibrin degradation generated in a moist wound environment and seen with some types of wound dressings. However, it is certainly not capable of removing devitalized tissue and therefore cannot serve as adequate replacement for surgical debridement. Therefore, there are no products that allow a correct debridement without invasive procedures and patient discomfort.

Wound care dressings (20) are very important for chronic wounds treatment given the morbidity associated with them. However, all wound care dressings are not active products (they cannot accelerate the healing process) and only help to protect the wound while the healing process is occurring. Besides, none of them can be used indistinctly in any kind of chronic wound because of the following problems: 1) A limited amount of exudate retained on the wound allows for autolytic debridement, which serves to further promote successful wound healing. Traditional dry gauze wound dressings (i.e Curity, Vaseline gauze, Xeroform) may degrade this process while also causing further injury when removed. 2) Low adherent dressings and semi permeable films (i.e. Bioclusive, Blisterfilm, Cutifilm, Flexigrid, OpSite, Tegaderm) represent the basic types of wound dressings with the goal of restricting liquid and microbial penetration but allowing air and water vapor through. Therefore, they can be only used for non-exudative wounds which represent the minority of them. 3) Hydrocolloids (i.e. Aquacel, Comfeel, DuoDERM, Granuflex, Tegasorb) can absorb a certain amount of exudate keeping a moist environment. However, because of its impermeable nature they prevent air exchange and should not be used on exudative wounds. Besides, it takes a long time between changes. 4) Hydrogels (i.e. Carrasyn, Curagel, Nu-Gel, Purilon, Restore, SAF-gel, XCell) may additionally be used to help promote moisture in an otherwise dry wound. They are easy to remove and change but may cause overhydration and therefore delaying healing. 5) Alginate dressings (i.e. Algisite, Kaltostat, Sorbsan, Tegagen) are seaweed-derived non-woven fibers that are generally reserved for highly exudative wounds because of their ability to absorb large amounts of fluid. As such, adverse effects can be seen in dry wounds dressed with alginate, for example they can be hemostatic (21). 6) Hydrofiber (i.e Aquacel Hydrofiber) with similar properties and adverse effects than alginate dressings. 7) Foams (i.e. 3M Adhesive Foam, Allevyn, Lyofoam, Tielle) minimize trauma during dressing changes but have limited absorptive capacity and can be used only on moderately exudative wounds. 8) There are combinations of traditional wound dressings such as foams or hydrogels with antimicrobial compounds such as silver, betaine, chitin, or polyhexamethylene biguanide (Kendall AMD). These materials may not be appropriate for broad-spectrum application to healing wounds but may be appropriate in chronic lower leg ulcers where infection can be a problem, especially with formation of biofilms. However, they can inhibit biofilm formation but they cannot produce biofilm disruption which is the true therapeutic requirement. 9) Collagen products: They have been used on recalcitrant wounds and chronic ulcers. It is thought to help facilitate an environment attracting cell types critical to wound healing while depleting negative effectors such as free radicals and proteases (22). However, this collagen is not intended to be a direct replacement for new production of collagen in wounded tissue (as it can be derived from multiple sources, including bovine and porcine collagen). Besides, they are not useful in infected wounds.

Skin substitutes (7) generally consist of a biologically derived substance combined with a material to allow for its placement on a wound. Overall, these dressings are quite costly, representing a significant barrier to widespread adoption. Besides, they represent high risk of infections and antigenicity. Several skin substitutes could be find in Market: 1) While multiple options have focused on a mesh material coated with porcine collagen or polypeptides (Biobrane and TransCyte), the latter of which also contains newborn fibroblast cells or a porcine xenograft (EZ Derm). However, they demonstrate to be cost-effective only for facial burns and not for general application. 2) Dermagraft is a material developed using fibroblasts derived from newborn foreskin tissue, extracellular matrix, and a bioabsorbable polyglactin mesh. However, it showed a high risk of rejection and hypersensitivity (as bovine serum may be contained in trace amounts in the preparation). 3) Apligraf, an allogenic bilayer cultured skin equivalent, where a dermal layer of cultured fibroblasts and bovine type I collagen is combined with an epidermal layer of cultured keratinocytes. This comes at a significant cost, however, as a single application of Apligraf can cost over US$1000 for a 7.5-cm-diameter circular disk and it can be cost effective only for recalcitrant, chronic, non-healing wounds, somewhat limiting the applicability in general of these products. 4) Omnigraft is an acellular bilayer matrix consisting of collagen, glycosaminoglycan, and chondroitin-6-sulfate, with a layer of silicone for barrier function. However, Omnigraft should not be used in patients with known sensitivity to bovine collagen or chondroitin materials and certainly should not be used on clinically diagnosed infected wounds.

Vacuum-assisted closure (VAC) (8) by maintaining a moist environment, optimizing blood flow, removing exudates, and applying pressure to promote wound closure, these devices are able to mitigate numerous factors that may be deficient in a chronic wound. However, it can be dangerous if negative-pressure dressings are placed directly in contact with exposed blood vessels, bones or nerves. Besides, it is contraindicated when osteomyelitis is present, or the patient has allergies or sensitivity to acrylic adhesives.

Growth factors (9), since a chronic wound contains so many perturbations in growth factors and cytokines, addressing some of these issues may be helpful. However, an environment where so many factors are deficient and dysregulated, simply replacing one is unable to rescue the chronic wound phenotype. In fact, the only one of these therapies proven to improve healing in a double-blinded randomized controlled trial is platelet-derived growth factor (PDGF) (Regranex becaplermin) and those results were rather modest.

Despide wound oxygenation being one of the most important therapeutic targets for chronic wounds, there are no products that increase vascularization by increase in situ vascular endothelial growth factor (VEGF).

Hyperbaric oxygen (10) has been used in wound healing on the basis of the principle that it can promote fibroblast proliferation, enhance immune function, and stimulate angiogenesis, among other functions. However, these ideals have not necessarily borne out in practice, leading to some degree of controversy in its use. Importantly, this therapy is applied to the patient in a hyperbaric oxygen chamber as localized delivery of oxygen has not been shown to be effective, which could lead to significant side effects including myopia, oxygen toxicity in the brain leading to seizures, and pneumothorax.

Several invention patents could be found that teach particular approaches such as AR093779 whose some inventors are the same as those of the present invention: This application teaches a supernatant of a *Lactobacillus* ferment that is proposed successfully in the treatment of chronic wounds (23-25). In this document, we will call the above-mentioned supernatant "LAPS". The technical problem with this supernatant is that since it is a fermentation supernatant, it comprises an indeterminate and variable composition according to the production conditions. In addition, it has limited stability over time, since there is evidence that its therapeutic function does not exceed 60 days.

EP 0848 951 B1 provides the use of N-acetyl cysteine (NAC) for the preparation of a composition for the treatment or prophylaxis of chronic wounds selected from the group consisting of diabetic foot ulcers and pressure sores wherein the composition is in the form of an ointment for topical administration to the chronic ulcer and the ointment comprises: 1) 0.01 to 1% w/w of NAC or pharmaceutical acceptable salt or derivatives thereof and 2) A carrier: Hydrogels containing cellulose (i.e. Hydroxyethylcellulose), hydrogels of polyacrylic acid (i.e. carbopol) or creams/ointments used for pharmaceutical preparations (i.e. cetomacrogol). The above carriers may include alginates, as thickener or stimulant, preservatives (i.e. benzyl alcohol), buffers to control pH (i.e. $Na_2HPO_4/NaH_2PO_4$), agents to adjust osmolarity (i.e. NaCl), stabilisers (i.e. EDTA). The claimed composition for chronic wound treatment that is based in NAC shows a pro-healing action by inhibiting MMPs. However, in their procedure 1, they demonstrate that NAC shows a concentration dependent inhibition of Intercellular adhesion molecule-1 (ICAM-1) expression. This is not something desirable for chronic wound treatment as it was previously demonstrated that wound healing is delayed in the absence of ICAM-1 (26).

U.S. Pat. No. 9,211,305 B2 teaches a composition of glycosaminoglycans for the treatment of diabetic foot ulcer, it specifically relates to low molecular weight heparins (LMWHs) and very low molecular weight heparins (VLMWHs) in the treatment of chronic ulcers, particularly of diabetic foot ulcers, and more specifically in the manufacture of a medicinal product for the treatment of chronic ulcers, and particularly diabetic foot ulcers and pressure ulcers. Specifically, this patent claims a method for treating chronic wounds but this treatment does not offer antimicrobial properties (bacteriostatic, bactericide, anti-biofilm), neither antioxidant or angiogenic properties. Therefore it must be used combined with other products.

U.S. Pat. No. 10,285,938 B2 Antimicrobial peptides represent a relatively new discovery in the immune system pathway. Recent designs of synthetically engineered antimicrobial peptides have demonstrated increased potency and efficacy/tolerability, enhanced specificity, and reduced toxicity in comparison. One such peptide, XYLENTRA®, has shown significant promise from significant in vitro studies against large+pathogens. Additionally, extensive animal studies have shown that the XYLENTRA® is an antimicrobial peptide against a large number of pathogens. The XYLENTRA® peptide is also solute resistant. The peptide XYLENTRA® has shown significant antibacterial activity on test organisms *Staphylococcus aureus* MTCC 96 and *Pseudomonas aeruginosa*. MTCC741. A substantial decrease in the microbial population level was observed in animals treated with peptide using the protocol described in detail in the application. Specifically, they claim a method of treating a wound that uses the aforementioned antimicrobial peptide. However, this method does not contemplate pro-healing properties like antioxidation, MMPs inhibition, angiogenesis, etc. Besides regarding their antimicrobial properties, they do not demonstrate effectiveness against biofilm (inhibition and/or disruption). Therefore it must be used combined with other products.

WO 2019/193333A1 relates to pharmaceutical composition comprising Triclosan (2,4,4 trichloro hydroxy diphenyl ether) and a thickener for use in treatment of chronic wounds and in particular in treating diabetic foot ulcers. Specifically, a topical composition with antimicrobial properties related to Triclosan. The active pro healing ingredient: Castor oil, Jojoba oil, Aloe Vera 10:1; Active antimicrobial ingredient: Triclosan; Emulsifiers: Stearic acid, GMSSE, Cetyl palmitate, Silicone fluid 200 100 CS, Liquid paraffin heavy, Monopropilenglicol. Gelificant: Carbopol 980 5%, Trietha-nolamine, Optional preservative: Nipastat However, this composition does not contemplate pro-healing properties like antioxidation, MMPs inhibition, angiogenesis, etc. Besides regarding their antimicrobial properties, they do not demonstrate effectiveness against biofilm (inhibition and/or disruption). Therefore it must be used combined with other products.

There are many authors that ensure that targeting oxidative stress is a key factor in the treatment of impaired wound healing (27-29). In this regard, there are two types of antioxidants that can be applied in vivo, antioxidant enzymes (such as SOD, catalase, peroxidase, and glutathione peroxidase) and nonenzymatic antioxidants (such as vitamin C, nitric oxide, metal-binding protein, etc) (27). However, most clinical trials with antioxidants were limited to oral administrations. For example it has been studied the influence of orally supplemented ascorbic acid on healing (28, 29). On the other hand, it has been proposed the topical application of antioxidants from plant extracts or enzymatic antioxidants in hydrogels for chronic wound treatment (27). The only reported clinical trial where a nonenzymatic antioxidant was applied locally on chronic wounds have been performed with a cream containing 5% DMSO, a potent Reactive oxygen species (ROS) scavenger and this treatment was not able to decrease ulcer occurrence (31). Moreover, a detrimental effect was noted on the incidence of heel and ankle injuries. The authors proposed several hypotheses to explain this unexpected result, in particular they evoked the possible pro-oxidant activity of DMSO (31). At physiological concentrations, DMSO and ascorbic acid are potent free radical scavengers in the plasma, protecting cells against oxidative damage caused by ROS (32).

Ajwee D M et al. (2012) teaches that Ethosuximide and phenobarbital promote wound healing via enhancing collagenization (33). They applied ethosuximide (Etho) to excisional wounds in Albino rats model. They demonstrate that ethosuximide-containing ointments 10% w/w (80 mg/mL) in soft paraffin significantly promotes wound healing by enhancing collagenization. They applied 150 mg of the ointment per day. It means 15 mg of Etho per day. Taking into account that Albino rats had a weight of 140 to 180 g and that the reference volemia of these animals is 50 mL per kilogram, then these rats had an aproximated volemia of 10 mL. If we consider that 100% of the daily applied Etho translocated to the bloodstream, then the first day of treatment Etho reaches a plasmatic concentration of 15 mg/10 mL. It means 1.5 mg/mL or 1500 ug/mL. In humans, the accepted therapeutic level is 40 to 100 ug/mL (See Zarontin prospect FDA). Above this concentration, hepatotoxicity, leukopenia, thrombocytopenia, sedation, and nausea are observed. Besides, this composition has not demonstrated antimicrobial properties (bacteriostatic, bactericide, anti-biofilm). Therefore it must be used combined with other products for wound treatment.

Goldberg S R et al. in their review (2020) indicates that there are five key points that become wounds chronic (34):
1) Ischemia. Ischemia produces tissue injury, necrosis, and the development of open wounds that are quickly colonized by bacteria.
2) Infection. Infection sets the stage for chronic and uncontrolled inflammation. Most chronic wounds are polymicrobial in nature with a preponderance of *Staphylococcus* and *Pseudomonas* species.
3) Biofilms formation. The proinflammatory response is perpetuated by the formation of a biofilm that walls off and protects the bacteria and the inflamed ulcer site. Biofilms stimulate the host immune response while directly resist antimicrobial therapy and stimulate chronic inflammation.
4) Chronic inflammation and tissue damage. As the host's inflammatory cells try to remove the damaged tissue, reactive oxygen species and proteases like MMPs are released, causing further tissue damage. Overexpression of MMPs causes damage to the extracellular matrix and drives the underlying pathology of chronic, non healing wounds. Overproduction of MMPs also destroys vital growth factors such as platelet-derived growth factor and transforming growth factor-b necessary for wound healing.
5) Decreased mitogenic activity. Because of the raging inflammatory environment, residual connective tissue cells have decreased mitogenic activity and become senescent.

Goldberg et al. indicates that this vicious cycle of inflammation and tissue destruction persists until aggressive clinical strategies are used to remove bacteria, damaged and necrotic tissue and reduce inflammation. They also indicate that in the state of technique the best approach to managing a patient's wounds is the DIME support products and services wound care guideline (35). This guideline consists of a comprehensive approach to assess a wound and recognize all products and services that are necessary to use at the same time to increase therapeutic effectivity. As it can be seen in this guideline, there is no product in the market with the capability to offer the 5 key points indicated by Goldberg at the same time (35).

That is why current treatments usually use a combination of therapies for wound infection, wound debridement and wound care. These kinds of products do not ensure healing and physicians must often recur to use also skin substitutes, vacuum assisted closure, growth factors and hyperbaric therapy. However none of them can offer all mentioned therapeutic requirements at the same time and therefore they also show a relative therapeutic efficacy.

Experts indicate that therapeutic effectivity will increase when therapies include at the same time all the following therapeutic requirements (36):
a) management of infection and biofilm elimination (37, 38),
b) management of exudate in quantity and composition (39),
c) specific growth factors reconstitution (9),
d) management of inflammation (4) and its deleterious effect, like accumulation of matrix metalloproteinases (40) and oxidative stress (29) and
e) pain control (41).

The present invention resolves the problems described in the state of Art by providing a composition for chronic wounds treatment that provides at the same time angiogenesis, broad spectrum bacteriostatic, bactericide, biofilm inhibition and biofilm disruption (including the most isolated bacteria in chronic wounds *S. aureus* and *P. aeruginosa*), Matrix metalloproteinases (MMPs) inhibition (through it acidification and chelating properties), collagen and alpha actin formation in the wound bed and pro-healing properties.

Besides, the present invention provides a composition for chronic wound treatment that surprisingly shows functional synergies produced by the combination of its components.

The present invention provides a composition and formulations comprising components for pharmacological use which, in combination, constitute a solution to the problem of the therapeutic treatment of chronic wounds. Solving the problems posed in the state of the art technology.

It is an object of the present invention to provide a composition for the treatment of wounds.

It is also an object of the present invention to provide a composition for the treatment of chronic wounds.

It is also an object of the present invention to provide a composition for the treatment of chronic wounds, comprising venous ulcers, arterial ulcers, pressure ulcers (bedsores); diabetic foot ulcers and mechanical or post-surgical wounds chronified by superinfection with biofilm-forming bacteria.

It is also an object of the present invention to provide formulations for topical delivery for in situ preparation.

It is also an object of the present invention to provide in situ preparation gel formulations for the treatment of wounds.

It is also an object of the present invention to provide a process to elaborate said composition.

It is also an object of the present invention to provide a device that enables in situ preparation gel formulations for the treatment of wounds.

It is also an object of the present invention to provide a method for treating a mammal with chronic wounds, comprising venous ulcers, arterial ulcers, pressure ulcers (bedsores); diabetic foot ulcers and mechanical or post-surgical wounds chronified by superinfection with biofilm-forming bacteria.

BRIEF DESCRIPTION

Figure 1:
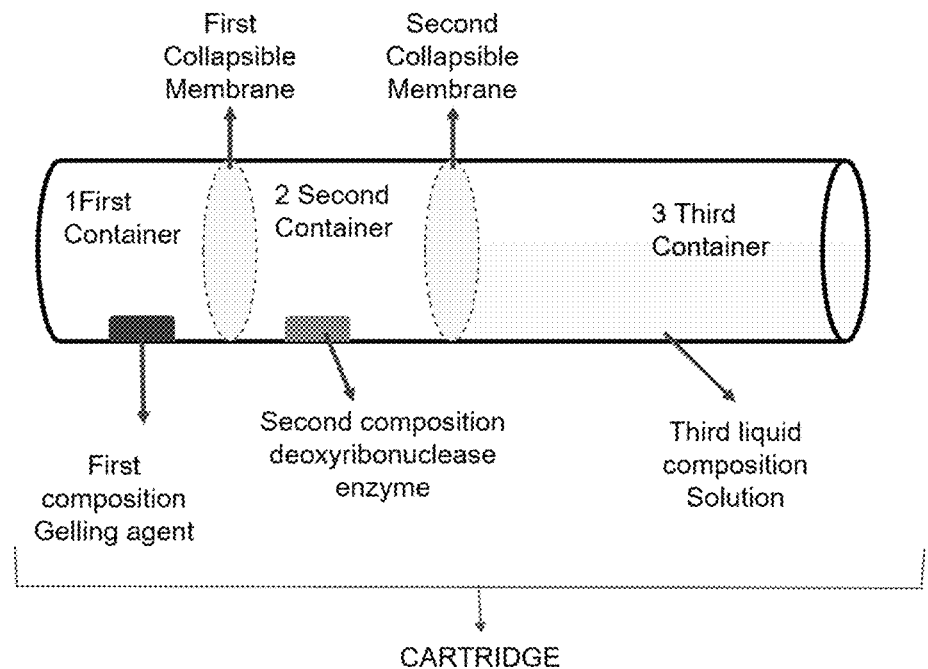
FIG. 1: Diagram of the device that contains formulation of the invention. It shows three containers separated by two collapsible membranes that allow the isolation of each composition. When the membranes are broken, container compositions are mixed.

In one aspect of the present invention, provided herein is a pharmaceutical composition for topical wound treatment comprising at least a nitrogenous heterocyclic compound of 5 or 6 atoms with imide group; one or more deoxyribonuclease enzyme with activity pH between 4.5 and 6.5; and one or more carboxylic acid. Wherein the nitrogenous heterocyclic compound of 5 or 6 atoms with imide group comprises a nitrogenous heterocyclic compound of 5 or 6 atoms with imide group selected from the group consisting of ethosuximide, barbituric acid, phenobarbital, 5,5-diethyl barbituric acid, 5-Ethyl-5-(1-methylbutyl) barbituric acid, pentobarbitone, pentobarbital, Nembutal, 5-Ethyl-5-(1-methylpropyl) barbituric acid, Butobarbital, butisol, 5-Allyl-5-(1-methylbutyl) -barbituric acid, secobarbital, Seconal, Phenytoin, Hydantoin and, and a mixture thereof; wherein, preferably, nitrogenous heterocyclic compound of 5 or 6 atoms with imide group is ethosuximide. Wherein the deoxyribonuclease enzyme comprises a deoxyribonuclease enzyme selected from the group consisting of DNase, rh-dornase alfa, bovine pancreatic DNase I, DNase II, prokaryotic DNase II or eukaryotic DNase II, DNase II alfa, DNase II beta, porcine spleen DNase II, and a mixture thereof; wherein, preferably, deoxyribonuclease enzyme is recombinant human Dornase-alpha. Wherein the carboxylic acid comprises an carboxylic acid selected from the group consisting of citric acid, lactic acid, acetic acid, formic acid, malic acid, tartaric acid, salicylic acid, oxalic acid, benzoic acid, propionic acid, and a mixture thereof; wherein, preferably, carboxylic acid is lactic acid.

In another embodiment of present invention said pharmaceutical composition further comprises one or more tensioactive agent selected from the group consisting of polysorbate 20, polysorbate 80, polysorbate 60, sorbitan triestearate, sorbitan monostearate, octoxynol-9, nonoxynol-9, and a mixture thereof; wherein, preferably, tensioactive agent is polysorbate 80.

In another embodiment of present invention said pharmaceutical composition further comprises one or more complex forming acid selected from the group consisting of ethylene glycol tetra acetic acid, ethylenediaminetetraacetic acid, dimercaptosuccinic acid, 2,3-Dimercapto-1-propanesulfonic acid, lipoic acid (1,2-dithiol-3-valeric acid), oxalic acid, and a mixture thereof; wherein, preferably, complex forming acid is ethylenediaminetetraacetic acid.

In another embodiment of present invention said pharmaceutical composition further comprises one or more hydrophilic reducing acid selected from the group consisting of uric acid, ascorbic acid, lipoic acid and a mixture thereof; wherein, preferably, hydrophilic reducing acid is ascorbic acid.

In another embodiment of present invention said pharmaceutical composition further comprises one or more gelling agent selected from the group consisting of cellulose, nano-crystalline cellulose, bacterial cellulose, hydroxyethyl cellulose, hydroxypropyl cellulose, microcrystalline cellulose, carboxymethyl cellulose, carbopol and a mixture thereof; wherein, preferably, gelling agent is hydroxyethyl cellulose.

In another embodiment of present invention said pharmaceutical composition further comprises a solution selected from the group consisting of acetic acid 0.2M/sodium acetate 0.2M: Ratio 2.78 to 0.66% (v/v) pH=4.2 to 4.8; acetic acid 0.10 M/sodium acetate 0.01 M: Ratio 1.05 to 10.05% (v/v) pH=5.6; monobasic potassium phosphate 0.05M pH=4.5; monobasic potassium phosphate 0.36 M/disodium phosphate 0.07M: Ratio 4.92 to 0.98% (p/v) pH=5.7; monobasic potassium phosphate 0.36 M/disodium phosphate 0.10M: Ratio 4.92 to 1.49% (p/v) pH=6.0; citric acid 0.31 M/disodium phosphate 0.20 M: Ratio 2.99 to 1.42% (p/v) pH=5.8; citric acid 0.10 M/sodium citrate 0.03

M: Ratio 1.92 a 0.77% (p/v) pH=5.8; Sørensen's phosphate buffer: sodium monobasic phosphate 0.2M/Disodium phosphate 2.3 M: Ratio 1.2 to 16.33% (p/v) pH=5.8; Hank's balanced salt solution (HBSS): sodium chloride 0.14 M (0.800%), potassium chloride 5 mM (0.040%), Calcium chloride 1 mM (0.014%), Magnesium sulphate heptahydrate 0.4 mM (0.010%), Magnesium chloride hexahydrate 0.5 mM (0.010%), Disodium phosphate dihydrate 0.3 mM (0.006%), Potassium monobasic phosphate 0.4 mM (0.006%), Glucose 6 mM (0.100%), Sodium bicarbonate 4 mM (0.035%): pH=5.7; 4-(2-hydroxyethyl)-1-piperazineethanesulfonic acid (HEPES) 1M (pH=6.5); 2-(N-Morpholino)ethanesulfonic acid sodium salt,4-Morpholineethanesulfonic acid (MES sodium salt) 0.5 M (pH 5.5-6.7); N,N-Bis(2-hydroxyethyl)-2-aminoethanesulfonic acid sodium salt (BES) 0.5 M (pH=6.0); N-(2-Acetamido)-2-aminoethanesulfonic acid (ACES) 0.5 M (pH=6.0); 2,2'-[(2-Amino-2-oxoethyl)imino]diacetic acid (ADA) 0.2 M (pH=6.0); piperazine-N,N'-bis(2-ethanesulfonic acid) (PIPES) 0.5 M (pH=6.0-6.8); 3-Morpholino-2-hydroxypropanesulfonic acid (MOPSO) 0.2 M (pH=6.0); saline solution (0.9%)/MgCL2 (5 mM). pH 5.5; 1M NaHCO3 solution and combinations thereof.

In another embodiment of present invention said pharmaceutical composition comprises a pH between about 4.5 and about 6.8.

In another embodiment of present invention said pharmaceutical composition comprises from about 0.5 to about 50 mg/ml one or more nitrogenous heterocyclic compound of 5 or 6 atoms with imide group; preferably from about 0.5 to about 30 mg/ml; more preferably from about 0.5 to about 3 mg/ml.

In another embodiment of present invention said pharmaceutical composition comprises from about 0.5 to about 4000 µg/ml one or more deoxyribonuclease enzyme; more preferably from about 1 to about 1000 µg/ml; more preferably from about 1 to about 4 µg/ml, more preferably from about 0.97 to about 3.9 µg/ml.

In another embodiment of present invention said pharmaceutical composition comprises from about 1 to about 15 mg/ml one or more carboxylic acid, more preferably from about 1 to about 9 mg/ml, more preferably from about 1.6 to about 9 mg/ml.

In another embodiment of present invention said pharmaceutical composition comprises about 5 mg/ml or less one or more tensioactive agents, more preferably about 3 mg/ml or less.

In another embodiment of present invention said pharmaceutical composition comprises about 1 mg/ml or less one or more complex forming acid, more preferably about 0.75 mg/ml or less.

In another embodiment of present invention said pharmaceutical composition comprises about 3 mg/ml or less one or more hydrophilic reducing acid, more preferably about 2.5 mg/ml or less.

In another embodiment of present invention said pharmaceutical composition comprises about 25 mg/ml or less one or more gelling agents, more preferably about 17 mg/ml or less.

In a particularly preferred embodiment of the present invention the pharmaceutical composition comprises ethosuximide, recombinant human Dornase-Alpha and lactic acid in solution.

In a particularly preferred embodiment of the present invention the pharmaceutical composition comprises ethosuximide, recombinant human Dornase-Alpha, lactic acid hydrophilic reducing acid, polysorbate 80, ascorbic acid, ethylenediaminetetraacetic acid, hydroxyethyl cellulose and a solution comprising saline solution 0.9% and $MgCl_2$ 5 mM at pH 5.5.

In a particularly preferred embodiment of the present invention the pharmaceutical composition comprises an aqueous solution of: from about 0.5 to about 30 mg/ml ethosuximide; from about 1 to about 4 µg/ml recombinant human Dornase-alpha; from about 1 to about 9 mg/ml lactic acid; about 2.5 mg/ml or less ascorbic acid; about 3 mg/ml or less polysorbate-80; about 0.75 mg/ml or less ethylenediaminetetraacetic acid; about 17 mg/ml or less hydroxyethyl cellulose.

In a particularly preferred embodiment of the present invention the pharmaceutical composition comprises an aqueous solution of: from about 0.5 to about 3 mg/ml ethosuximide; from about 0.97 to about 3.9 µg/ml recombinant human Dornase-alpha; from about 1.6 to about 8.7 mg/ml lactic acid; about 2.5 mg/ml or less ascorbic acid; about 3 mg/ml or less polysorbate-80; about 0.75 mg/ml or less ethylenediaminetetraacetic acid; about 17 mg/ml or less hydroxyethyl cellulose.

In a particularly preferred embodiment of the present invention the pharmaceutical formulation kit for topical wound treatment comprising a first composition and a second composition that are mixed before use to obtain the composition of the invention, wherein: the first composition is solid and comprises a deoxyribonuclease enzyme and a gelling agent powder; and the second composition is an aqueous liquid comprising an at least one nitrogenous heterocyclic compound of 5 or 6 atoms with imide group and at least one carboxylic acid; and the second composition has a pH between 4.5 and 6.8.

In a particularly preferred embodiment of the present invention the pharmaceutical formulation kit for topical wound treatment comprises a first composition, a second composition, and a third composition that are mixed before use, wherein: the first composition is solid and comprises a gelling agent powder; the second composition is solid and comprises a deoxyribonuclease enzyme; and the third composition is an aqueous liquid comprising an at least one nitrogenous heterocyclic compound of 5 or 6 atoms with imide group and an at least one carboxylic acid; and the third composition has a pH between 4.5 and 6.8.

In another embodiment of present invention the pharmaceutical formulation kit comprising the first composition, the second composition and the third composition, each one contained in a hermetic and separate container.

Another object of the present invention is a process for preparing said pharmaceutical formulation that comprises the steps of:
  a. put in contact the first composition with the second composition;
  b. mix and shake obtaining gel pharmaceutical composition.

Another object of the present invention is a process for preparing the composition of invention from the pharmaceutical formulation of invention comprising a first composition, a second composition, and a third composition that are mixed before use, wherein the first composition is solid and comprises a gelling agent powder; the second composition is solid and comprises a deoxyribonuclease enzyme; and the third composition is an aqueous liquid comprising at least one nitrogenous heterocyclic compound of 5 or 6 atoms with imide group and at least one carboxylic acid; and the third composition has a pH between 4.5 and 6.8 comprising:

a. put in contact the third composition with the second composition;
b. mix and shake the third composition with the second composition;
c. put in contact the first composition with the mix obtained in step b.;
d. mix and shake obtaining gel pharmaceutical composition Another object of the present invention is a method for treating a wound of a mammal comprising applying the pharmaceutical composition of the invention to the wound at least once a day.

In another embodiment of present invention said wound is a wound selected from the group consisting of a diabetic foot ulcer, a venous ulcer, an arterial ulcer, a pressure ulcers, a mechanical wound characterized by a superinfection with a biofilm-forming bacteria, a post-surgical wound characterized by a superinfection with a biofilm-forming bacteria, and a combination thereof.

Another embodiment of present invention is a device comprising the pharmaceutical formulation of the invention, comprising:
a first container comprising a first composition; and
a second container comprising a second composition,
wherein the first container and the second container are separated by a collapsible membrane capable of keeping the first composition and the second composition isolated.
Another embodiment of present invention is a device comprising the pharmaceutical formulation of the invention, comprising:
a first container comprising a first composition;
a second container comprising a second composition; and
a third container comprising a third composition,
wherein:
the first container and the second container are separated by a first collapsible membrane capable of keeping the first composition and the second composition isolated; and
the second container and the third container are separated by a second collapsible membrane capable of keeping the second composition and the third composition isolated.

Another embodiment of present invention is a process for producing the pharmaceutical composition of the invention comprising the following steps:
a. mixing in a solution a nitrogenous heterocyclic compound of 5 or 6 atoms with imide group, a deoxyribonuclease enzyme, and carboxylic acid, thereby forming a mixture;
b. adding an alkaline solution dropwise to the mixture until the pH of the mixture is between 4.50 and 6.50, thereby forming a pH-adjusted mixture; and
c. sterilizing the pH-adjusted mixture. Wherein further comprising the step:
d. adding a gelling agent.
Wherein further comprising the step:
e. adding a complex forming acid, tensioactive agent and hydrophilic reducing acid.

DETAILED DESCRIPTION

The present invention provides a pharmaceutical composition and formulations and a kit for the topical treatment of wounds that achieves a multiplicity of technical effects, mainly therapeutic effects.

Wounds that are likely to be treated with this invention are chronic ulcers refractory to conventional healing treatments such as venous ulcers, arterial ulcers, pressure ulcers (bedsores); diabetic foot ulcers and mechanical or post-surgical wounds chronified by superinfection with biofilm-forming bacteria.

The term "nitrogenous heterocyclic compound of 5 or 6 atoms with imide group" as used in the present document refers to any chemical compound pharmaceutically acceptable that has a chemical 5 or 6 atoms ring in which almost 1 of those atoms is "N" and is part of an imide group. The Imide group is —CO—NH—CO—. Examples of nitrogenous heterocyclic compound of 5 or 6 atoms with imide group of some embodiments of the present disclosure are, without limitation, ethosuximide, barbituric acid, phenobarbital, 5,5-diethyl barbituric acid (barbital or veronal), 5-Ethyl-5-(1-methylbutyl) barbituric acid (Pentobarbitone, Pentobarbital or Nembutal), 5-Ethyl-5-(1-methylpropyl) barbituric acid (Butabarbital, butisol), 5-Allyl-5-(1-methylbutyl)-barbituric acid (secobarbital or seconal), Phenytoin, Hydantoin and combinations thereof. Ethosuximide has been used for the examples of this invention, but any pharmaceutically acceptable nitrogenous heterocyclic compound of 5 or 6 atoms with imide group compound listed above could be equivalent.

The term "carboxylic acid" as used in the present document refers to any carboxylic acid pharmaceutically acceptable. Examples of carboxylic acid of some embodiments of the present disclosure are, without limitation, citric acid, lactic acid, acetic acid, formic acid, malic acid, tartaric acid, salicylic acid, oxalic acid, benzoic acid, propionic acid and combinations thereof. Lactic acid has been used for the examples of this invention, but any pharmaceutically acceptable carboxylic acid listed above could be equivalent.

The term "deoxyribonuclease enzyme" as used in the present document refers to any pharmaceutically acceptable deoxyribonuclease enzyme with activity pH between 4.5 and 6.5. Examples of deoxyribonuclease enzymes of some embodiments of the present disclosure are, without limitation, DNase I of any origin: prokaryotic or eukaryotic. For example recombinant human DNase or rh-dornase alfa and bovine pancreatic DNase I; DNase II of any origin: prokaryotic or eukaryotic. For example: DNase II alfa, DNase II beta and porcine spleen DNase II, and combinations thereof. rh-dornase alfa has been used for the examples of this invention, but any pharmaceutically acceptable deoxyribonuclease enzyme listed above could be equivalent.

The term "hydrophilic reducing acid" as used in the present document refers to any hydrophilic reducing acid pharmaceutically acceptable. Examples of hydrophilic reducing acid of some embodiments of the present disclosure are, without limitation, uric acid, ascorbic acid, lipoic acid and combinations thereof. Ascorbic acid has been used for the examples of this invention, but any pharmaceutically acceptable hydrophilic reducing acid listed above could be equivalent.

The term "complex forming acid" as used in the present document refers to any complex forming acid pharmaceutically acceptable. Examples of complex forming acid of some embodiments of the present disclosure are, without limitation, ethylene glycol tetraacetic acid (EGTA), ethylenediaminetetraacetic acid (EDTA), dimercaptosuccinic acid (DMSA), 2,3-Dimercapto-1-propanesulfonic acid (DMPS), lipoic acid (1,2-dithiol-3-valeric acid), oxalic acid and combinations thereof. EDTA has been used for the examples of this invention, but any pharmaceutically acceptable complex forming acid listed above could be equivalent.

The term "tensioactive agent" as used in the present document refers to any pharmaceutically acceptable surfactant. Examples of tensioactive agents of some embodiments of the present disclosure are, without limitation, polysorbate 20, polysorbate 80, polysorbate 60, sorbitan triestearate, sorbitan monostearate, octoxynol-9, nonoxynol-9 ethoxylated castor oil at 40 moles of ethylene oxide, ethoxylated lauric alcohol of from 7 to 10 moles, Cremophor Kolliphor, Lipocol oxo 650, Solutol HS 15, Emulgin B1 PH, Lanette 20 PH, Polysorbate, Polysorbate 20, Polysorbate 60, Polysorbate 80, ethoxylated fatty alcohols (of from 6 to 30 moles of ethylene oxide) derived from Capri alcohol, decyl alcohol, lauryl alcohol, isotridecyl alcohol, myristyl alcohol, ethyl alcohol, palmoleyl, stearyl, oleyl, elaidyl, petroselinyl, linolyl alcohol, linolenic, elaeostearyl alcohol, eicosyl, arachyl, gadoleyl, behenyl alcohol, erucyl alcohol, brassidyl and combinations thereof. Polysorbate 80 has been used for the examples of this invention, but any pharmaceutically acceptable tensioactive agent listed above could be equivalent.

The term "gelling agent" as used in the present document refers to any pharmaceutically acceptable gel-forming agent that when is dissolved in a liquid phase as a colloidal mixture forms a weakly cohesive internal structure. Examples of gelling agent of some embodiments of the present disclosure are, without limitation, cellulose, nanocrystalline cellulose, bacterial cellulose, hydroxypropyl cellulose, microcrystalline cellulose, carbopol, cellulose derivative, ethylcellulose, hydroxyethylcellulose, guar gum, gum arabic, hydroxyethylmethylcellulose, hydroxyethylpropylcellulose, carboxymethylcellulose, xanthan gum, chitosan, alginate, gelatin, sodium starch glycolate, sodium corscarmelosa, alginic acid, pectin and combinations thereof. Hydroxyethyl cellulose has been used for the examples of this invention, but any pharmaceutically acceptable gelling agent listed above could be equivalent.

The present invention is a pharmaceutical composition for topical wound treatment that comprises at least three components in a solution. The concentrations of said components are in mg/ml, meaning mg of component/ml of said solution and in % w/v meaning % weight of component/volume of said solution.

The term "solution" or "MS" or "Mixing Solvent" as used indistinctly in the present document refers to any pharmaceutically acceptable aqueous solvent. Examples of pharmaceutically acceptable aqueous solvent of some embodiments of the present disclosure are, without limitation, acetic acid 0.2M/sodium acetate 0.2M: Ratio 2.78 to 0.66% (v/v) pH=4.2 to 4.8; acetic acid 0.10 M/sodium acetate 0.01 M: Ratio 1.05 to 10.05% (v/v) pH=5.6; monobasic potassium phosphate 0.05M pH=4.5; monobasic potassium phosphate 0.36 M/disodium phosphate 0.07M: Ratio 4.92 to 0.98% (p/v) pH=5.7; monobasic potassium phosphate 0.36 M/disodium phosphate 0.10M: Ratio 4.92 to 1.49% (p/v) pH=6.0; citric acid 0.31 M/disodium phosphate 0.20 M: Ratio 2.99 to 1.42% (p/v) pH=5.8; citric acid 0.10 M/sodium citrate 0.03 M: Ratio 1.92 a 0.77% (p/v) pH=5.8; Sørensen's phosphate buffer: sodium monobasic phosphate 0.2M/Disodium phosphate 2.3 M: Ratio 1.2 to 16.33% (p/v) pH=5.8; Hank's balanced salt solution (HBSS): sodium chloride 0.14 M (0.800%), potassium chloride 5 mM (0.040%), Calcium chloride 1 mM (0.014%), Magnesium sulphate heptahydrate 0.4 mM (0.010%), Magnesium chloride hexahydrate 0.5 mM (0.010%), Disodium phosphate dihydrate 0.3 mM (0.006%), Potassium monobasic phosphate 0.4 mM (0.006%), Glucose 6 mM (0.100%), Sodium bicarbonate 4 mM (0.035%): pH=5.7; 4-(2-hydroxyethyl)-1-piperazineethanesulfonic acid (HEPES) 1M (pH=6.5); 2-(N-Morpholino)ethanesulfonic acid sodium salt,4-Morpholineethanesulfonic acid (MES sodium salt) 0.5 M (pH 5.5-6.7); N,N-Bis(2-hydroxyethyl)-2-aminoethanesulfonic acid sodium salt (BES) 0.5 M (pH=6.0); N-(2-Acetamido)-2-aminoethanesulfonic acid (ACES) 0.5 M (pH=6.0); 2,2'-[(2-Amino-2-oxoethyl)imino]diacetic acid (ADA) 0.2 M (pH=6.0); piperazine-N,N'-bis(2-ethanesulfonic acid) (PIPES) 0.5 M (pH=6.0-6.8); 3-Morpholino-2-hydroxypropanesulfonic acid (MOPSO) 0.2 M (pH=6.0); saline solution (0.9%)/MgCL2 (5 mM). pH 5.5; 1M NaHCO3 solution and combinations thereof. Saline solution (0.9%)/MgCL2 (5 mM) at pH 5.5 has been used for the examples of this invention, but any pharmaceutically acceptable solution or MS listed above could be equivalent. The solution used for the examples of present invention, that is de mixing solvent (MS) is a saline solution (0.9%) and 5 mM of $MgCl_2$ at pH 5.5.

The composition of the invention is bactericide but could be formulated with a pharmaceutical acceptable preservative selected from the group consisting of Benzyl Alcohol, Benzoic Acid, Methyl Hydroxybenzoate, Propyl Hydroxybenzoate, Benzalkonium chloride, Chlorocresol, Phenylmercuric Nitrate, Chlorobutanol, Sodium Dehydroacetate, Thimerosal, Sodium Benzoate, Sorbic Acid and combinations thereof.

The composition of the invention could be formulated with a pharmaceutical acceptable anesthetic selected from the group consisting of lidocaine, pramoxine, benzocaine, between others and combinations thereof Among the technical effects achieved by this invention it is possible to detail the following:

Bacteriostatic and bactericidal effect: Existing products on the market have only a reduced spectrum of activity, while the composition of the present invention is capable of eliminating 99% of planktonic strains isolated from chronic wounds. This effect is not achieved by any of the state-of-the-art products, therefore currently; more than one product must be used.

Inhibitory effect of bacterial biofilm formation: Existing inhibitor products only inhibit one bacterial strain at a time while the composition of this invention inhibits the formation of 99% biofilm of strains isolated from chronic wounds.

Disruptive effect of preformed bacterial biofilm: The bacteria biofilm disrupting products on the market only cause the breakdown of the biofilm of a single species at a time, while the composition of this invention causes the biofilm disruption of 95% of the most isolated strains of chronic wounds, including mixed biofilms (formed by more than one species as in vivo), for which there are no products on the market.

Debriding effect: The composition of this invention removes the fibrin/biofilm/necrotic tissue layer from the wound surface.

Inhibitory effect of wound enlargement: This effect is achieved through the inhibition of MMPs and free radicals that causes the composition of this invention. It also does it through the pharmaceutical form absorbing the exudate. There are no products on the market for this purpose.

Oxygenating effect: The oxygenating power of the present invention is achieved through induction of the expression of vascular endothelial growth factor (VEGF) that stimulates angiogenesis. The elimination of aerobic pathogenic flora also increases the $pO_2$ in the wound.

Collagenizing effect: The present invention stimulates the formation and deposition of collagen in the ulcer bed.

The composition of this invention presents an extended stability compared to the state of art as it has been demonstrated that it is active at least for 6 months.

A device for containing the formulation of the present invention is another objective of the present invention. Said device, in one embodiment, comprises three containers: a first container that stores a first composition, a second container that stores a second composition and a third container that stores the third composition. Wherein the first composition is solid and comprises a gelling agent powder; the second composition is solid and comprises a deoxyribonuclease enzyme and the third composition is an aqueous solution comprising an at least one nitrogenous heterocyclic compound of 5 or 6 atoms with imide group and at least one carboxylic acid; and the third composition has a pH between 4.5 and 6.8. The third composition could further comprise one or more hydrophilic reducing acid; one or more tensioactive agent; one or more complex forming acid.

One embodiment of present invention provides a device of thee containers wherein the first container and the second container are separated by a first collapsible membrane capable of keeping the first composition and the second composition isolated; and the second container and the third container are separated by a second collapsible membrane capable of keeping the second composition and the third composition isolated.

The term "collapsible membrane" as used in the present document refers to any membrane or film made of rigid or flexible material that is collapsible, breakable, frangible, tearable or removable, to separate said containers. These collapsible membranes are made from any material known in the Art such as polymer, aluminum, silicon, for example. When the collapsible membrane separating adjacent containers is broken, the compositions in said containers are brought into contact.

The term "container" as used in the present document refers to any container that contains a composition isolated from the ambient and from other compositions. This container could share a collapsible membrane with another container that, when this membrane is broken, said compositions contained in those containers are brought into contact. The containers of present invention could be independent and isolated containers or could be part of a single device with two or three containers that share collapsible membranes between them, as can be seen in FIG. 1.

The device of present invention is a cartridge or a dispenser.

One embodiment provides a dispenser device with a nozzle, which can include a removable cap.

An exemplary device is shown in FIG. 1. This multicompartment device is a cylindrical cartridge of rigid material. Materials useful for making this device disclosed herein include high barrier polypropylene, aluminium, glass, between others, for preventing moisture and oxygen exposure. Two collapsible membranes divide this exemplary device in three containers. This collapsible membrane could be broken by pressure or with any system to break a film, known in the art.

Another objective of present invention is a process for preparing the pharmaceutical composition of invention in-situ before use in wound treatment. This process comprises the following steps:
a. put in contact the third composition with the second composition, breaking the second collapsible membrane;
b. mix and shake the third composition with the second composition;
c. put in contact the first composition with the mix obtained in step b. breaking the first collapsible membrane;
d. mix and shake obtaining gel pharmaceutical composition of invention.

In step a., a perfect mix is possible: the enzyme of the second composition in the second container is distributed in all the volume when is shaken with the third liquid aqueous composition of the third container. This mixture from step a is combined with a gelling agent of the first composition in the first container, in step c, and are shaken to obtain a homogeneous gel composition of the invention.

One embodiment provides a device for containing the formulation of the present invention. Said device comprises two containers: a first container that stores a first composition, and a second container that stores a second composition. Wherein the first composition is solid and comprises a gelling agent powder and a deoxyribonuclease enzyme, and the second composition is an aqueous solution comprising an at least one nitrogenous heterocyclic compound of 5 or 6 atoms with imide group and at least one carboxylic acid; and the third composition has a pH between 4.5 and 6.8. The third composition could further comprises one or more hydrophilic reducing acid; one or more tensioactive agent; one or more complex forming acid.

The formulation of this invention that is prepared in situ previous to the application would present an expiration date similar to the used enzyme.

The stability over time for the formulation of the invention contained in the device of the invention, with two or three containers is about two years. This stability is that of enzyme used, since it is in the form of a lyophilized powder in an isolated container or compartment without being in contact with the solution. Therefore, the formulation of the invention in its device of the invention presents an extended stability compared to the state of art. And when the formulation is prepared, putting in contact the first composition with the second composition and with the third composition (when the device presents 3 containers) and it is shaken to mix all compositions, the gel prepared presents a stability of about 6 months or more.

EXEMPLARY EMBODIMENTS

Example 1

Component Solutions Preparation

Solutions of the different components of the present invention composition were prepared.

Mixing solvent (MS): Saline solution (0.9%)/$MgCL_2$ (5 mM). pH 5.5

A liter of solution is prepared weighing 9.0000 g of Sodium Chloride and 1.0106 g of Magnesium Chloride hexahydrate ($MgCl_2.6\,H_2O$) and dissolving them in distilled water.

Alkaline solution: A 1M NaHCO3 solution. In a volumetric flask, 100 ml of solution is prepared dissolving 8.4 g of Sodium Bicarbonate in distilled water. It is important to dissolve the Sodium bicarbonate completely with the solvent in a beaker to avoid supersaturation before to make up to the mark in the flask. Final pH of the alkaline solution is approximately: 8.6.

Lactic acid solution in mixing solvent (LA). LA is diluted in the mentioned mixing solvent and then is mixed for a few minutes. The final pH=5.5 is reached with alkaline solution. The concentrations prepared were: LA 1.63 mg/mL, LA 6.50 mg/mL, LA 8.67 mg/mL.

Polysorbate 80 solution in mixing solvent (PS80). PS80 is diluted and then is mixed for a few minutes until the homogenization is reached. The final pH=5.5 is reached using alkaline solution. The concentrations prepared were: PS80 2.0 mg/mL, PS80 3.0 mg/mL.

EDTA solution in mixing solvent: EDTA is dissolved in the mentioned mixing solvent and then is mixed for a few minutes. The final pH=5.5 is reached using alkaline solution. The concentrations prepared were: EDTA 0.25 mg/mL, EDTA 0.50 mg/mL, EDTA 0.75 mg/mL.

Ascorbic acid solution in mixing solvent (AA). AA is dissolved in the mentioned solvent mixture and then is mixed for a few minutes. The final pH=5.50 is reached using alkaline solution. The concentrations prepared where: AA 0.5 mg/mL, AA 1.0 mg/mL, AA 2.50 mg/mL.

Ethosuximide solution in mixing solvent (Etho). Etho is dissolved in mixing_solvent and then is mixed for a few minutes. The final pH=5.5 is reached using alkaline solution. The concentrations prepared were: Etho 0.50 mg/mL, Etho 3.00 mg/mL, Etho 30.00 mg/mL.

rh-Dornase alfa solution in mixing solvent (D1). D1 is dissolved in mixture solvent and then is mixed for a few minutes. The final pH=5.5 is reached with alkaline solution. The concentrations prepared were: D1 250 µg/mL, D1 125 µg/mL, D1 62.5 µg/mL, D1 31.2 µg/mL, D1 15.6 µg/mL, D1 7.8 µg/mL, D1 3.9 µg/mL, D1 1.9 µg/mL, D1 0.97 µg/mL, D1 0.5 µg/mL.

*Lactobacillus plantarum* supernatant of 24 hours (LAPS 24 h) control: *L. plantarum* ATCC 10241 was grown for 12 hours in de Man Rogosa Sharpe (MRS) (Britania. Argentina) at 37° C. Supernatant (LAPS) was obtained by centrifugation for 15 min at 8000 rpm and filtration with Millipore filters of 0.22 µm. Then the preparation was stored at 2-8° C. for 24 hours. To obtain the pharmaceutical form in gel, Hydroxyethyl cellulose 1.7% was adding.

*Lactobacillus plantarum* supernatant of 6 months (LAPS 6m) control: preparations of LAPS 24 h were stored at 2-8° C. for 6 months before being used.

Example 2

Composition of the Invention. Preparation of the Mixture No. 0 (M0) in the Laboratory The composition of the invention is composed of:
a. 6.50 mg/mL lactic acid (85%-90% purity)
b. 3.00 mg/mL Ethosuximide
c. DNase (rh-Dornase alfa) 0.97 µg/ml
Solution: The mixture is formulated (a+b+c)
In 50 ml of mixing solvent, 150 mg of ethosuximide, 318 µl of lactic acid and 50 µg of rh-Dornase alfa enzyme are added.

Preparation Mode 1. 150 mg of ethosuximide is weighed on watch glass with analytical balance Radwag AS 220 R2 (Radwag LLC, Radom, Poland).
2. With the help of the mixing solvent this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.
4. Next, 318 µl of lactic acid are added to the preparation.
5. Once these substances are added, the mixture is left stirring for an extra 5 minutes.
6. The solution is brought to a final pH of 5.5, placing 50 mL of solution in a 100 mL beaker and the Lutron PH-206 pH meter electrode previously calibrated (Lutron Electronics Co. Inc., Pennsylvania, USA) is immersed in it.
7. The assembly is placed on a stirrer at low revolutions and the alkaline solution is added dropwise until pH 5.5 is reached, being careful with the effervescence generated by its aggregate.
8. The preparation is sterilized in autoclave Arcano LS-B75L at 120° C. at 1 atm overpressure for 10 min.
9. After sterilizing process finishing, 50 mL of the preparation is placed in conical tubes and 50 µg of rh-Dornase alfa enzyme (Roche, Basel, Switzerland) is added under sterile conditions to achieve a final concentration of 0.97 µg/mL. This step is performed in a biological safety cabinet.
10. The tube is sealed and mixed in a vortex for 1 minute.
11. The preparation is isolated from the light using aluminum foil and then stored at 4° C.-25° C.

Example 3

Composition of the Invention. Preparation of the Mixture No. 13 (M13) in the Laboratory The composition of the invention comprises:
a. 3.00 mg/mL Polysorbate 80
b. 1.00 mg/mL ascorbic acid
c. 6.50 mg/mL lactic acid (85%-90% purity)
d. 0.50 mg/mL EDTA
e. 3.00 mg/mL ethosuximide
f. 0.97 µg/mL DNase
Solution: The mixture is formulated (a+b+c+d+e+f)
In 50 ml of mixing solvent are added: 50 mg of ascorbic acid, 25 mg of EDTA, 150 mg of ethosuximide, 50 µg of rh-Dornase alfa, 141 µl of Polysorbate 80 and 318 µl of lactic acid.

Preparation Mode:

1. 50 mg of ascorbic acid and 25 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved. During stirring, 141 µl of Polysorbate 80 is added with 200 µl tips by cutting the tip of it.
4. Next, 318 µl of lactic acid are added to the preparation.
5. 150 mg of ethosuximide are added.
6. Once these substances are added, the mixture is left stirring for an extra 5 minutes.
7. Said mixture is brought to a final pH of 5.5, placing 50 mL of mixture in a 100 mL beaker and the Lutron PH-206 pH meter electrode previously calibrated (Lutron Electronics Co. Inc., Pennsylvania, USA) is immersed in it.

8. The mixture of step 7 is placed on a stirrer at low revolutions and the alkaline solution is added dropwise until pH 5.5 is reached, being careful with the effervescence generated by its aggregate.
9. The mixture of step 8 is sterilized in autoclave Arcano LS-B75L at 120° C. at 1 atm overpressure for 10 min.
10. After sterilizing process finishing, 50 mL of the mixture is placed in 50 ml conical tubes and 50 µg of rh-Dornase alfa enzyme (Roche, Basel, Switzerland) is added under sterile conditions to achieve a final concentration of 0.97 µg/mL. This step is performed in a biological safety cabinet.
11. The tube is sealed and mixed in a vortex for 1 minute.
12. The composition of the invention of step 11 is isolated from the light using aluminum foil and then stored at 4° C.-25° C.

Example 4

Composition of the Invention. Preparation of the Mixture No. 15 (M15) in the Laboratory The composition of the invention comprises:
a. 2.00 mg/mL Polysorbate 80
b. 0.50 mg/mL ascorbic acid
c. 1.63 mg/mL lactic acid (85%-90% purity)
d. 0.25 mg/mL EDTA
e. 0.50 mg/mL ethosuximide
f. 3.90 µg/mL DNase
The mixture is formulated (a+b+c+d+e+f)
In 50 ml of mixture solvent are added: 25.00 mg of ascorbic acid, 12.50 mg of EDTA, 25 mg of ethosuximide, 200 µg of rh-Dornase alfa, 94 µl of Polysorbate 80 and 80 µl of lactic acid.

Preparation Mode 1. 25 mg of ascorbic acid and 12.50 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.
During stirring, 94 µl of Polysorbate 80 is added with 200 µl tips by cutting the tip of it.
4. Next, 80 µl of lactic acid is added to the preparation.
5. 25 mg of ethosuximide are added.
6. Once these substances are added, the mixture is left stirring for an extra 5 minutes.
7. Said mixture is brought to a final pH of 5.5, placing 50 mL of mixture in a 100 mL beaker and the Lutron PH-206 pH meter electrode previously calibrated (Lutron Electronics Co. Inc., Pennsylvania, USA) is immersed in it.
8. The mixture of step 7 is placed on a stirrer at low revolutions and the alkaline solution is added dropwise until pH 5.5 is reached, being careful with the effervescence generated by its aggregate.
9. The preparation is sterilized in autoclave Arcano LS-B75L at 120° C. at 1 atm overpressure for 10 min.
10. After sterilizing process finishing, 50 mL of the preparation solution is placed in 50 ml conical tubes and 200 µg of rh-Dornase alfa enzyme (Roche, Basel, Switzerland) is added under sterile conditions to achieve a final concentration of 3.90 µg/mL. This step is performed in a biological safety cabinet.
11. The tube is sealed and mixed in a vortex for 1 minute.
12. The composition of the invention of step 11 is isolated from the light using aluminum foil and then stored at 4° C.-25° C.

Example 5

Composition of the Invention Preparation of the Mixture No. 16 (M16) in the Laboratory The composition of the invention comprises:
a. 3.00 mg/mL Polysorbate 80
b. 2.50 mg/mL ascorbic acid
c. 8.67 mg/mL lactic acid (85%-90% purity)
d. 0.75 mg/mL EDTA
e. 30.00 mg/mL ethosuximide
f. 3.90 µg/mL DNase
The mixture is formulated (a+b+c+d+e+f)
In 50 ml of mixing solvent are added: 125 mg of ascorbic acid, 37.5 mg of EDTA, 1500 mg of ethosuximide, 200 µg of rh-Dornase alfa, 141 µl of Polysorbate 80 and 424 µl of lactic acid.

Preparation Mode 1. 125 mg of ascorbic acid and 37.5 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak TechnologY LLC, Dubai, UAE) for 5 min until the solid particles have partially dissolved. During stirring, 141 µl of Polysorbate 80 is added with 200 µl tips by cutting the tip of it.
4. Next, 424 µl of lactic acid is added to the preparation.
5. 1500 mg of ethosuximide are added.
6. Once these substances are added, the mixture is left stirring for an extra 5 minutes.
7. Lutron PH-206 pH meter electrode is calibrated (Lutron Electronics Co. Inc., Pennsylvania, USA) to measure the pH of the preparation.
8. The solution is brought to a final pH of 5.5, placing 50 mL of solution with the pH meter in a 100 mL beaker on a stirrer at low revolutions and adding the alkaline solution dropwise until pH level is reached being careful with the effervescence generated by its aggregate.
9. The preparation is sterilized in autoclave Arcano LS-B75L at 120° C. at 1 atm overpressure for 10 min.
10. After sterilizing process finishing, 50 mL of the preparation solution is placed in 50 ml conical tubes and 200 µg of rh-Dornase alfa enzyme (Roche, Basel, Switzerland) is added under sterile conditions to achieve a final concentration of 3.90 µg/mL. This step is performed in a biological safety cabinet.
11. The tube is sealed and mixed in a vortex for 1 minute.
12. The composition of the invention of step 11 is isolated from the light using aluminum foil and then stored at 4° C.-25° C.

Example 6

Composition of the Invention. Gel Preparation of the Mixture No. 0 (M0) in the Laboratory The composition of the invention is composed of:
a. 6.50 mg/mL lactic acid (85%-90% purity)
b. 3.00 mg/mL Ethosuximide
c. DNase 0.97 µg/ml
d. 17 mg/mL Hydroxyethyl cellulose
Solution: The mixture is formulated (a+b+c)
In 50 ml of mixing solvent, 150.0 mg of ethosuximide, 318 µl of lactic acid and 50 µg of rh-Dornase alfa enzyme are added.

Preparation Mode 1. 150.0 mg of ethosuximide is weighed on watch glass with analytical balance Radwag AS 220 R2 (Radwag LLC, Radom, Poland).
2. With the help of the mixing solvent this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak TechnologY LLC, Dubai, UAE) for 5 min until the solid particles have partially dissolved.
4. Next, 318 µl of lactic acid are added to the preparation.
5. Once these substances are added, the mixture is left stirring for an extra 5 minutes.
6. The solution is brought to a final pH of 5.5, placing 50 mL of solution in a 100 mL beaker and the Lutron PH-206 pH meter electrode previously calibrated (Lutron Electronics Co. Inc., Pennsylvania, USA) is immersed in it.
7. The assembly is placed on a stirrer at low revolutions and the alkaline solution is added dropwise until pH 5.5 is reached, being careful with the effervescence generated by its aggregate.
8. The preparation is sterilized in autoclave Arcano LS-B75L at 120° C. at 1 atm overpressure for 10 min.
9. After sterilizing process finishing, 50 mL of the preparation is placed in conical tubes and 50 µg of rh-Dornase alfa enzyme (Roche, Basel, Switzerland) is added under sterile conditions to achieve a final concentration of 0.97 µg/mL. This step is performed in a biological safety cabinet.
10. The tube is sealed and mixed in a vortex for 1 minute.
Gel: The mixture is formulated (Solution+d)
11. Add 0.85 g of Hydroxyethylcellulose to the prepared mixture.
12. Mix gently until homogeneous.
13. The preparation is isolated from light using aluminum foil, and then stored at 4-25° C. and covered. It should be left to rest between 6 and 8 hours until the bubbles are eliminated.

Example 7

Composition of the Invention. Gel Preparation of the Mixture No. 13 (M13) in the Laboratory The composition of the invention comprises:
a. 3.00 mg/mL Polysorbate 80
b. 1.00 mg/mL ascorbic acid
c. 6.50 mg/mL lactic acid (85%-90% purity)
d. 0.50 mg/mL EDTA
e. 3.00 mg/mL ethosuximide
f. 0.97 µg/mL DNase
g. 17 mg/mL Hydroxyethyl cellulose
Solution: The mixture is formulated (a+b+c+d+e+f)
In 50 ml of mixing solvent are added: 50 mg of ascorbic acid, 25 mg of EDTA, 150 mg of ethosuximide, 50 µg of rh-Dornase alfa, 141 µl of Polysorbate 80 and 318 µl of lactic acid.

Preparation Mode 1. 50 mg of ascorbic acid and 25 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak TechnologY LLC, Dubai, UAE) for 5 min until the solid particles have partially dissolved. During stirring, 141 µl of Polysorbate 80 is added with 200 µl tips by cutting the tip of it.
4. Next, 318 µl of lactic acid are added to the preparation.
5. 150 mg of ethosuximide are added.
6. Once these substances are added, the mixture is left stirring for an extra 5 minutes.
7. Said mixture is brought to a final pH of 5.5, placing 50 mL of mixture in a 100 mL beaker and the Lutron PH-206 pH meter electrode previously calibrated (Lutron Electronics Co. Inc., Pennsylvania, USA) is immersed in it.
8. The mixture of step 7 is placed on a stirrer at low revolutions and the alkaline solution is added dropwise until pH 5.5 is reached, being careful with the effervescence generated by its aggregate.
9. The mixture of step 8 is sterilized in autoclave Arcano LS-B75L at 120° C. at 1 atm overpressure for 10 min.
10. After sterilizing process finishing, 50 mL of the mixture is placed in 50 ml conical tubes and 50 µg of rh-Dornase alfa enzyme (Roche, Basel, Switzerland) is added under sterile conditions to achieve a final concentration of 0.97 µg/mL. This step is performed in a biological safety cabinet.
11. The tube is sealed and mixed in a vortex for 1 minute.
Obtaining gel: The mixture is formulated (Solution+g)
12. Add 0.85 of Hydroxyethylcellulose to the prepared mixture.
13. Mix gently until homogeneous.
14. The preparation is isolated from light using aluminum foil, and then stored at 4-25° C. and covered. It should be left to rest between 6 and 8 hours until the bubbles are eliminated.

Example 8

Composition of the Invention. Gel Preparation of the Mixture No. 15 (M15) in the Laboratory The composition of the invention comprises:
a. 2.00 mg/mL Polysorbate 80
b. 0.50 mg/mL ascorbic acid
c. 1.63 mg/mL lactic acid (85%-90% purity)
d. 0.25 mg/mL EDTA
e. 0.50 mg/mL ethosuximide
f. 3.90 µg/mL DNase
g. 17 mg/mL Hydroxyethyl cellulose The mixture is formulated (a+b+c+d+e+f)

In 50 ml of mixture solvent are added: 25.00 mg of ascorbic acid, 12.50 mg of EDTA, 25 mg of ethosuximide, 200 µg of rh-Dornase alfa, 94 µl of Polysorbate 80 and 80 µl of lactic acid.

Preparation Mode 1. 25 mg of ascorbic acid and 12.5 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.
During stirring, 94 µl of Polysorbate 80 is added with 200 µl tips by cutting the tip of it.
4. Next, 80 µl of lactic acid is added to the preparation.
5. 25 mg of ethosuximide are added.
6. Once these substances are added, the mixture is left stirring for an extra 5 minutes.
7. Said mixture is brought to a final pH of 5.5, placing 50 mL of mixture in a 100 mL beaker and the Lutron PH-206 pH meter electrode previously calibrated (Lutron Electronics Co. Inc., Pennsylvania, USA) is immersed in it.
8. The mixture of step 7 is placed on a stirrer at low revolutions and the alkaline solution is added dropwise until pH 5.5 is reached, being careful with the effervescence generated by its aggregate.
9. The preparation is sterilized in autoclave Arcano LS-B75L at 120° C. at 1 atm overpressure for 10 min.
10. After sterilizing process finishing, 50 mL of the preparation solution is placed in 50 ml conical tubes and 200 µg of rh-Dornase alfa enzyme (Roche, Basel, Switzerland) is added under sterile conditions to achieve a final concentration of 3.90 µg/mL. This step is performed in a biological safety cabinet.
11. The tube is sealed and mixed in a vortex for 1 minute. Obtaining gel: The mixture is formulated (Solution+g)
12. Add 0.85 g of Hydroxyethylcellulose to the prepared mixture.
13. Mix gently until homogeneous.
14. The preparation is isolated from light using aluminum foil, and then stored at 4-25° C. and covered. It should be left to rest between 6 and 8 hours until the bubbles are eliminated.

Example 9

Composition of the Invention. Gel Preparation of the Mixture No. 16 (M16) in the Laboratory The composition of the invention comprises:
a. 3.00 mg/mL Polysorbate 80
b. 2.50 mg/mL ascorbic acid
c. 8.67 mg/mL lactic acid (85%-90% purity)
d. 0.75 mg/mL EDTA
e. 30.00 mg/mL ethosuximide
f. 3.90 µg/mL DNase
g. 17 mg/mL Hydroxyethyl cellulose The mixture is formulated (a+b+c+d+e+f)

In 50 ml of mixing solvent are added: 125 mg of ascorbic acid, 37.5 mg of EDTA, 1500 mg of ethosuximide, 200 µg of rh-Dornase alfa, 141 µl of Polysorbate 80 and 424 µl of lactic acid.

Preparation Mode 1. 125 mg of ascorbic acid and 37.5 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved. During stirring, 141 µl of Polysorbate 80 is added with 200 µl tips by cutting the tip of it.
4. Next, 424 µl of lactic acid is added to the preparation.
5. 1500 mg of ethosuximide are added.
6. Once these substances are added, the mixture is left stirring for an extra 5 minutes.
7. Lutron PH-206 pH meter electrode is calibrated (Lutron Electronics Co. Inc., Pennsylvania, USA) to measure the pH of the preparation.
8. The solution is brought to a final pH of 5.5, placing 50 mL of solution with the pH meter in a 100 mL beaker on a stirrer at low revolutions and adding the alkaline solution dropwise until pH level is reached being careful with the effervescence generated by its aggregate.
9. The preparation is sterilized in autoclave Arcano LS-B75L at 120° C. at 1 atm overpressure for 10 min.
10. After sterilizing process finishing, 50 mL of the preparation solution is placed in 50 ml conical tubes and 200 µg of rh-Dornase alfa enzyme (Roche, Basel, Switzerland) is added under sterile conditions to achieve a final concentration of 3.90 µg/mL. This step is performed in a biological safety cabinet.
11. The tube is sealed and mixed in a vortex for 1 minute. Obtaining gel: The mixture is formulated (Solution+g)
12. Add 0.85 g of Hydroxyethylcellulose to the prepared mixture.
13. Mix gently until homogeneous.
14. The preparation is isolated from light using aluminum foil, and then stored at 4-25° C. and covered. It should be left to rest between 6 and 8 hours until the bubbles are eliminated.

Example 10

Composition of the Invention. Preparation of the Mixture No. 0 (M0) in Preferred Pharmaceutical Formulation The composition of the invention is composed of:
a. 6.5 mg/mL Lactic Acid (85%-90% purity)
b. 3.00 mg/mL Ethosuximide
c. 0.97 µg/mL DNAse
d. 17 mg/mL Hydroxyethyl Cellulose
Solution: The mixture is formulated (a+b); container 1 (d) and container 2 (c).

In 50 ml of mixing solvent, 150.0 mg of ethosuximide and 318 µl of lactic acid are added.

Preparation Mode 1. 150.0 mg of ethosuximide is weighed on watch glass with analytical balance Radwag AS 220 R2 (Radwag LLC, Radom, Poland).
2. With the help of the whole mixing solvent, this substance is eluted on a glass beaker so as not to leave any particles in the watch glass.
3. The beaker with the preparation is placed on a NUMAK GL-3250A magnetic stirrer (Numak Technology LLC, Dubai, UAE) for 5 min until the solid particles have partially dissolved.
4. Next, 318 µl of lactic acid are added into the preparation.
5. Once these substances are added, the mixture is left stirring for an extra 5 minutes.
6. Lutron PH-206 pH meter electrode is calibrated (Lutron Electronics Co. Inc., Pennsylvania, USA) to measure the pH of the preparation.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min and stored at 4-25° C., hermetically closed and saved from the light sources.

Pharmaceutical formulation: The preferred pharmaceutical form of the present invention is a gel. The gel is obtained after a two-stage process. The application device comprises three containers separated by two collapsible membranes. The formulation of invention comprises:

Container 1: This container is charged with 0.85 g of lyophilized Hydroxyethyl Cellulose in q.s. to obtain a gel with the expected rheological properties.

Container 2: In this container 50 µg of lyophilized rh-Dornase alfa are placed in q.s. to obtain a final solution of 0.97 µg/mL.

Container 3: In this container 50 mL of the preparation of step 8 are placed.

In the first mixing stage, membrane No. 2 is broken to allow the mixing of the contents of containers 2 and 3. The mixing improves the homogenization.

In the second mixing stage, membrane No. 1 is broken allowing the mixing of the homogenate with the container 1 content. This container has the excipient therefore in this stage the final pharmaceutical form of gel is achieved. The mixing improves the homogenization of all the components.

Example 11

Composition of the Invention. Preparation of the Mixture No. 13 (M13) in Preferred Pharmaceutical Formulation The composition of the invention comprises:
a. 3.00 mg/mL Polysorbate 80
b. 1.00 mg/mL ascorbic acid
c. 6.50 mg/mL lactic acid (85%-90% purity)
d. 0.50 mg/mL EDTA
e. 3.00 mg/mL ethosuximide
f. 0.97 µg/mL DNase
g. 17 mg/mL Hydroxyethyl Cellulose Solution: The mixture is formulated (a+b+c+d+e); container 1 (g) and container 2 (f).

In 50 ml of mixing solvent are added: 50 mg of ascorbic acid, 25 mg of EDTA, 150 mg of ethosuximide, 141 µl of Polysorbate 80 and 318 µl of lactic acid.

Preparation Mode 1. 50 mg of ascorbic acid and 25 mg of EDTA are weighed on watch glass.
2. The mixing solvent is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.

During stirring, 141 µl of Polysorbate 80 is added with 200 µl tips by cutting the tip of it.
4. Next, the volume 318 µl of lactic acid are added to the preparation.
5. The 150 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min and stored at 4-25° C., hermetically closed and saved from the light sources.

Pharmaceutical formulation: The preferred pharmaceutical form of the present invention is a gel. The gel is obtained after a two-stage process. The application device comprises three containers separated by two collapsible membranes. The formulation of invention comprises:

Container 1: This container is charged with 0.85 g of lyophilized Hydroxyethyl Cellulose in q.s. to obtain a gel with the expected rheological properties.

Container 2: In this Container 50 µg of lyophilized rh-Dornase alfa are placed in q.s. to obtain a solution of 0.97 µg/mL.

Container 3: In this container 50 mL of the preparation of step 8 are placed.

In the first mixing stage, membrane No. 2 is broken to allow the mixing of the contents of containers 2 and 3. The mixing improves the homogenization.

In the second mixing stage, membrane No. 1 is broken allowing the mixing of the homogenate with the container 1 content. This container has the excipient therefore in this stage the final pharmaceutical form of gel is achieved. The mixing improves the homogenization of all the components.

Example 12

Composition of the Invention Preparation of the Mixture No. 15 (M15) in Preferred Pharmaceutical Formulation The composition of the invention comprises:
a. 2.00 mg/mL Polysorbate 80
b. 0.50 mg/mL ascorbic acid
c. 1.63 mg/mL lactic acid (85%-90% purity)
d. 0.25 mg/mL EDTA
e. 0.50 mg/mL ethosuximide
f. 3.90 µg/mL DNase
g. 17 mg/mL Hydroxyethyl Cellulose Solution: The mixture is formulated (a+b+c+d+e)

In 50 ml of mixing solvent are added: 25 mg of ascorbic acid, 12mg of EDTA, 25 mg of ethosuximide, 94 µl of Polysorbate 80 and 80 µl of lactic acid.

Preparation Mode 1. 25 mg of ascorbic acid and 12.5 mg of EDTA are weighed on watch glass.
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.

During stirring, 94 µl of Polysorbate 80 is added with 200 µl tips by cutting the tip of it.

4. Next, the volume 80 µl of lactic acid is added to the preparation.
5. The 25 mg of ethosuximide are added.
6. Once these substances are added, the mixture is left stirring for an extra 5 minutes.
7. The solution is brought to a final pH of 5.5, placing 50 mL of solution with the pH meter in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min and stored at 4-25° C., hermetically closed and saved from the light sources.

Pharmaceutical formulation: The preferred pharmaceutical form of the present invention is a gel. The gel is obtained after a two-stage process. The application device comprises three containers separated by two collapsible membranes. The formulation of invention comprises:

Container 1: This container is charged with 0.85 g of lyophilized Hydroxyethyl Cellulose in q.s. to obtain a gel with the expected rheological properties.

Container 2: In this container 200 µg of lyophilized rh-Dornase alfa are placed in q.s. to obtain a solution of 3.90 µg/mL.

Container 3: In this container 50 mL of the preparation of step 8 are placed.

In the first mixing stage, membrane No. 2 is broken to allow the mixing of the contents of containers 2 and 3. The mixing improves the homogenization.

In the second mixing stage, membrane No. 1 is broken allowing the mixing of the homogenate with the container 1 content. This container has the excipient therefore in this stage the final pharmaceutical form of gel is achieved. The mixing improves the homogenization of all the components.

Example 13

Composition of the Invention Preparation of the Mixture No. 16 (M16) in Preferred Pharmaceutical Formulation The composition of the invention comprises:
a. 3.00 mg/mL Polysorbate 80
b. 2.50 mg/mL ascorbic acid
c. 8.67 mg/mL lactic acid (85%-90% purity)
d. 0.75 mg/mL EDTA
e. 30.00 mg/mL ethosuximide
f. 3.90 µg/mL DNase
g. 17 mg/mL Hydroxyethyl Cellulose Solution: The mixture is formulated (a+b+c+d+e)

In 50 ml of mixing solvent are added: 125 mg of ascorbic acid, 37.5 mg of EDTA, 1500 mg of ethosuximide, 141 µl of Polysorbate 80 and 424 µl of lactic acid.

Preparation Mode 1. 125 mg of ascorbic acid and 37.5 mg of EDTA are weighed on watch glass with analytical balance Radwag AS 220 R2 (Radwag LLC, Radom, Poland).
2. With the help of the solvent mixture, this substance is eluted on a glass beaker so as not to leave any particles in the watch glass.
3. After adding the rest of the 50 ml of the mixing solvent into the beaker, the preparation is placed on a NUMAK GL-3250A magnetic stirrer (Numak Technology LLC, Dubai, UAE) for 5 min until the solid particles have partially dissolved.

During stirring, 141 µl of Polysorbate 80 is added with 200 µl tips by cutting the tip of it.

4. Next, the volume 424 µl of lactic acid is added to the preparation.
5. The 1500 mg of ethosuximide are added.
6. Once these substances are added, the mixture is left stirring for an extra 5 minutes.
7. Mixture of step 6 is brought to a final pH of 5.5, placing 50 mL of solution with the pH meter Lutron PH-206 electrode in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min. and is stored after this step at 4-25° C., hermetically closed and saved from the light sources.

Pharmaceutical formulation: The preferred pharmaceutical form of the present invention is a gel. The gel is obtained after a two-stage process. The application device comprises three containers separated by two collapsible membranes. The formulation of invention comprises:

Container 1: This container is charged with 0.85 g of lyophilized Hydroxyethyl Cellulose in q.s. to obtain a gel with the expected rheological properties.

Container 2: In this container 200 µg of lyophilized rh-Dornase alfa are placed in q.s. to obtain a solution of 3.90 µg/mL.

Container 3: In this container 50 mL of the preparation of step 8 are placed.

In the first mixing stage, membrane No. 2 is broken to allow the mixing of the contents of containers 2 and 3. The mixing improves the homogenization.

In the second mixing stage, membrane No. 1 is broken allowing the mixing of the homogenate with the container 1 content. This container has the excipient therefore in this stage the final pharmaceutical form of gel is achieved. The mixing improves the homogenization of all the components.

Example 14

Composition of the Invention. Preparation of the Mixture No. 0 (M0) in Preferred Pharmaceutical Formulation The composition of the invention comprises:
a. 6.50 mg/mL lactic acid (85%-90% purity)
b. 3.00 mg/mL ethosuximide
c. 0.97 µg/mL DNase
d. 17 mg/mL Hydroxyethyl Cellulose
Solution: The mixture is formulated (a+b)
In 50 ml of mixing solvent are added: 150 mg of ethosuximide and 318 µl of lactic acid.

Preparation Mode 1. 150.0 mg of ethosuximide is weighed on watch glass with analytical balance Radwag AS 220 R2 (Radwag LLC, Radom, Poland).
2. With the help of the whole mixing solvent, this substance is eluted on a glass beaker so as not to leave any particles in the watch glass.
3. The beaker with the preparation is placed on a NUMAK GL-3250A magnetic stirrer (Numak Technology LLC, Dubai, UAE) for 5 min until the solid particles have partially dissolved.
4. Next, 318 µl of lactic acid are added into the preparation.
5. Once these substances are added, the mixture is left stirring for an extra 5 minutes.
6. The solution is brought to a final pH of 5.50, placing 50 mL of solution with calibrated Lutron PH-206 pH meter electrode in a 100 mL beaker on a stirrer at low revolutions and adding the alkaline solution dropwise until pH level is reached being careful with the effervescence generated by its aggregate.
7. The preparation is sterilized in autoclave Arcano LS-B75L at 120° C. at 1 atm overpressure for 10 min. and is stored at 4-25° C., hermetically closed and saved from the light sources.

Pharmaceutical form: The preferred pharmaceutical form of the present invention is a gel. The gel is obtained after a one-stage process. The application device comprises two containers separated by one collapsible membrane. The formulation of the present invention comprising:

Container 1: In this container 50 mL of the preparation of step 7 are placed.

Container 2: In this container 50 µg of lyophilized rh-Dornase alfa are placed in q.s. to obtain a solution of 0.97 µg/mL and 0.85 g of lyophilized Hydroxyethyl Cellulose in q.s. to obtain a gel with the expected rheological properties.

In the mixing process, the collapsible membrane is broken to allow the mixing of the contents of containers 1 and 2. The mixing allows achieving the final pharmaceutical form and improves the homogenization of all the components.

Example 15

Composition of the Invention Preparation of the Mixture No. 13 (M13) in Preferred Pharmaceutical Formulation The composition of the invention is composed of:
a. 3.00 mg/mL Polysorbate 80
b. 1 mg/mL ascorbic acid
c. 6.50 mg/mL lactic acid (85%-90% purity)
d. 0.50 mg/mL EDTA
e. 3.00 mg/mL ethosuximide
f. 0.97 µg/mL DNase
g. 17 mg/mL Hydroxyethyl Cellulose
Solution: The mixture is formulated (a+b+c+d+e)
In 50 ml of mixing solvent are added: 50 mg of ascorbic acid, 25 mg of EDTA, 150 mg of ethosuximide, 141 µl of Polysorbate 80 and 318 µl of lactic acid.

Preparation Mode 1. 50 mg of ascorbic acid and 25 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak TechnologY LLC, Dubai, UAE) for 5 min until the solid particles have partially dissolved.

During stirring, 141 µl of Polysorbate 80 is added with 200 µl tips by cutting the tip of it.

4. Next, the volume 318 µl of lactic acid is added to the preparation.
5. The 150 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min and stored at 4-25° C., hermetically closed and saved from the light sources.

Pharmaceutical form: The preferred pharmaceutical form of the present invention is a gel. The gel is obtained after a one-stage process. The application device comprises two containers separated by one collapsible membrane. The formulation of the present invention comprising:

Container 1: In this container 50 mL of the preparation of step 8 are placed.

Container 2: In this container 50 µg of lyophilized rh-Dornase alfa are placed in q.s. to obtain a solution of 0.97 µg/mL and 0.85 g of lyophilized Hydroxyethyl Cellulose in q.s. to obtain a gel with the expected rheological properties.

In the mixing process, the collapsible membrane is broken to allow the mixing of the contents of containers 1 and 2. The mixing allows achieving the final pharmaceutical form and improves the homogenization of all the components.

Example 16

Composition of the Invention Preparation of the Mixture No. 15 (M15) in Preferred Pharmaceutical Formulation The composition of the invention comprises:
a. 2.00 mg/mL Polysorbate 80
b. 0.50 mg/mL ascorbic acid
c. 1.63 mg/mL lactic acid (85%-90% purity)
d. 0.25 mg/mL EDTA
e. 0.50 mg/mL ethosuximide f. 3.90 µg/mL DNase
g. 17 mg/mL Hydroxyethyl Cellulose Solution: The mixture is formulated (a+b+c+d+e)

In 50 ml of mixing solvent are added: 25 mg of ascorbic acid, 12.5 mg of EDTA, 25 mg of ethosuximide, 94 µl of Polysorbate 80 and 80 µl of lactic acid.

Preparation Mode 1. 25 mg of ascorbic acid and 12.5 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak TechnologY LLC, Dubai, UAE) for 5 min until the solid particles have partially dissolved.

During stirring, 94 µl of Polysorbate 80 is added with 200 µl tips by cutting the tip of it.

4. Next, the volume 80 µl of lactic acid is added to the preparation.
5. The 25 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min and stored at 4-25° C., hermetically closed and saved from the light sources.

Pharmaceutical form: The preferred pharmaceutical form of the present invention is a gel. The gel is obtained after a one-stage process. The application device comprises two containers separated by one collapsible membrane. The formulation of the present invention comprising:

Container 1: In this container 50 mL of the preparation of step 8 are placed.

Container 2: In this container 200 µg of lyophilized rh-Dornase alfa are placed in q.s. to obtain a solution of 3.90 µg/mL and 0.85 g of lyophilized Hydroxyethyl Cellulose in q.s. to obtain a gel with the expected rheological properties.

In the mixing process, the collapsible membrane is broken to allow the mixing of the contents of containers 1 and 2. The mixing allows achieving the final pharmaceutical form and improves the homogenization of all the components.

Example 17

Composition of the Invention Preparation of the Mixture No. 16 (M16) in Preferred Pharmaceutical Formulation The composition of the invention is composed of:
a. 3.00 mg/mL Polysorbate 80
b. 2.50 mg/mL ascorbic acid
c. 8.67 mg/mL lactic acid (85%-90% purity)
d. 0.75 mg/mL EDTA
e. 30.00 mg/mL ethosuximide
f. 3.90 µg/mL DNAse
g. 17 mg/mL Hydroxyethyl Cellulose Solution: The mixture is formulated (a+b+c+d+e)

In 50 ml of mixing solvent are added: 125 mg of ascorbic acid, 37.5 mg of EDTA, 1500 mg of ethosuximide, 141 µl of Polysorbate 80 and 424 µl of lactic acid.

Preparation Mode 1. 125 mg of ascorbic acid and 37.5 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.

During stirring, 141 µl of Polysorbate 80 is added with 200 µl tips by cutting the tip of it.

4. Next, the volume 424 µl of lactic acid is added to the preparation.
5. The 1500 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min and stored at 4-25° C., hermetically closed and saved from the light sources.

Pharmaceutical form: The preferred pharmaceutical form of the present invention is a gel. The gel is obtained after a one-stage process. The application device comprises two containers separated by one collapsible membrane. The formulation of the present invention comprising:

Container 1: In this container 50 mL of the preparation of step 8 are placed.

Container 2: In this container 200 µg of lyophilized rh-Dornase alfa are placed in q.s. to obtain a solution of 3.90 µg/mL and 0.85 g of lyophilized Hydroxyethyl Cellulose in q.s. to obtain a gel with the expected rheological properties.

In the mixing process, the collapsible membrane is broken to allow the mixing of the contents of containers 1 and 2. The mixing allows achieving the final pharmaceutical form and improves the homogenization of all the components.

Example 18

Composition of the Invention. Preparation of the Mixture No. 0 (M0) in the Laboratory The composition of the invention comprises:
a. 6.50 mg/mL lactic acid (85%-90% purity)
b. 3.00 mg/mL ethosuximide
c. 0.97 µg/mL DNAse Solution: The mixture is formulated (a+b+c)

In 50 ml of mixing solvent are added: 150 mg of ethosuximide, 50 µg of rh-Dornase alfa, and 318 µl of lactic acid.

Preparation Mode 1. 150.0 mg of ethosuximide is weighed on watch glass with analytical balance Radwag AS 220 R2 (Radwag LLC, Radom, Poland).

2. With the help of the whole mixing solvent, this substance is eluted on a glass beaker so as not to leave any particles in the watch glass.
3. The beaker with the preparation is placed on a NUMAK GL-3250A magnetic stirrer (Numak Technology LLC, Dubai, UAE) for 5 min until the solid particles have partially dissolved.
4. Next, 318 µl of lactic acid are added into the preparation.
5. Once these substances are added, the mixture is left stirring for an extra 5 minutes.
6. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
7. The preparation is sterilized in autoclave Arcano LS-B75L at 120° C. at 1 atm overpressure for 10 min.
8. 50 mL of preparation of step 7 is placed in conical tubes (50 ml) and 0.05 mL of Dornase alfa 1 mg/mL enzyme Pulmozyme (Roche, Basel, Switzerland) is added under sterile conditions to achieve a final concentration of 0.97 µg/ml. This step is performed in a biological safety cabinet.
9. Once sealed the tube is mixed in vortex for 10 seconds.
10. The preparation is isolated from the light using aluminum foil and then stored at 4° C.-25° C.

Example 19

Composition of the Invention. Preparation of the Mixture No. 13 (M13) in the Laboratory The composition of the invention comprises:
a. 3.00 mg/mL Polysorbate 80
b. 1 mg/mL ascorbic acid
c. 6.50 mg/mL lactic acid (85%-90% purity)
d. 0.50 mg/mL EDTA
e. 3.00 mg/mL ethosuximide
f. 0.97 µg/mL DNase
Solution: The mixture is formulated (a+b+c+d+e+f)
In 50 ml of mixing solvent are added: 50 mg of ascorbic acid, 25 mg of EDTA, 150 mg of ethosuximide, 50 µg of rh-Dornase alfa, 141 µl of Polysorbate 80 and 318 µl of lactic acid.

Preparation Mode 1. 50 mg of ascorbic acid and 25 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.
During stirring, 141 µl of Polysorbate 80 is added with 200 µl tips by cutting the tip of it.
4. Next, the volume 318 µl of lactic acid is added to the preparation.
5. The 150 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min.
9. 50 mL of preparation of step 8 is placed in conical tubes (50 ml) and 0.05 mL of Dornase alfa 1 mg/mL enzyme Pulmozyme (Roche, Basel, Switzerland) is added under sterile conditions to achieve a final concentration of 0.97 µg/ml. This step is performed in a biological safety cabinet.
10. Once sealed the tube is mixed in vortex for 10 seconds.
11. The preparation is isolated from the light using aluminum foil and then stored at 4° C.-25° C.

Example 20

Composition of the Invention Preparation of the Mixture No. 15 (M15) in the Laboratory The composition of the invention is composed of:
a. 2.00 mg/mL Polysorbate 80
b. 0.50 mg/mL ascorbic acid
c. 1.63 mg/mL lactic acid (85%-90% purity)
d. 0.25 mg/mL EDTA
e. 0.50 mg/mL ethosuximide
f. 3.90 µg/mL DNase
Solution: The mixture is formulated (a+b+c+d+e+f)
In 50 ml of mixing solvent are added: 25 mg of ascorbic acid, 12.5 mg of EDTA, 25 mg of ethosuximide, 200 µg of rh-Dornase alfa, 94 µl of Polysorbate 80 and 80 µl of lactic acid.

Preparation Mode 1. 25 mg of ascorbic acid and 12.5 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.
During stirring, 94 µl of Polysorbate 80 is added with 200 µl tips by cutting the tip of it.
4. Next, the volume 80 µl of lactic acid is added to the preparation.
5. The 25 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min
9. 50 mL of preparation of step 8 is placed in conical tubes (50 ml) and 0.20 ml of Dornase alfa 1 mg/mL enzyme Pulmozyme (Roche, Basel, Switzerland) is added under sterile conditions to achieve a final concentration of 3.90 μg/ml. This step is performed in a biological safety cabinet.
10. Once sealed the tube is mixed in vortex for 10 seconds.
11. The preparation is isolated from the light using aluminum foil and then stored at 4° C.-25° C.

Example 21

Composition of the Invention Preparation of the Mixture No. 16 (M16) in the Laboratory The composition of the invention comprises:
a. 3.00 mg/mL Polysorbate 80
b. 2.50 mg/mL ascorbic acid
c. 8.67 mg/mL lactic acid (85%-90% purity)
d. 0.75 mg/mL EDTA
e. 30.00 mg/mL ethosuximide
f. 3.90 μg/mL DNase
Solution: The mixture is formulated (a+b+c+d+e+f)
In 50 ml of mixing solvent are added: 125 mg of ascorbic acid, 37.5 mg of EDTA, 1500 mg of ethosuximide, 200 μg of rh-Dornase alfa, 141 μl of Polysorbate 80 and 424 μl of lactic acid.

Preparation Mode 1. 125 mg of ascorbic acid and 37.50 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.
During stirring, 141 μl of Polysorbate 80 is added with 200 μl tips by cutting the tip of it.
4. Next, the volume 424 μl of lactic acid is added to the preparation.
5. The 1500 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min.
9. 50 mL of preparation of step 8 is placed in conical tubes (50 ml) and 0.20 ml of Dornase alfa 1 mg/mL enzyme Pulmozyme (Roche, Basel, Switzerland) is added under sterile conditions to achieve a final concentration of 3.90 μg/mL. This step is performed in a biological safety cabinet.
10. Once sealed the tube is mixed in vortex for 10 seconds.
11. The preparation is isolated from the light using aluminum foil and then stored at 4° C.-25° C.

Example 22

Gel composition of the Invention. Preparation of the Mixture No. 0 (M0) in the Laboratory The composition of the invention comprises:
a. 6.50 mg/mL lactic acid (85%-90% purity)
b. 3.00 mg/mL ethosuximide
c. 0.97 μg/mL DNase
d. 17 mg/mL Hydroxyethyl Cellulose
Solution: The mixture is formulated (a+b+c)
In 50 ml of mixing solvent are added: 150 mg of ethosuximide, 50 μg of rh-Dornase alfa, and 318 μl of lactic acid.

Preparation Mode 1. 150.0 mg of ethosuximide is weighed on watch glass with analytical balance Radwag AS 220 R2 (Radwag LLC, Radom, Poland).
2. With the help of the whole mixing solvent, this substance is eluted on a glass beaker so as not to leave any particles in the watch glass.
3. The beaker with the preparation is placed on a NUMAK GL-3250A magnetic stirrer (Numak TechnologY LLC, Dubai, UAE) for 5 min until the solid particles have partially dissolved.
4. Next, 318 μl of lactic acid are added into the preparation.
5. Once these substances are added, the mixture is left stirring for an extra 5 minutes.
6. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
7. The preparation is sterilized in autoclave Arcano LS-B75L at 120° C. at 1 atm overpressure for 10 min.
8. 50 mL of preparation of step 7 is placed in conical tubes (50 ml) and 0.05 mL of Dornase alfa 1 mg/mL enzyme Pulmozyme (Roche, Basel, Switzerland) is added under sterile conditions to achieve a final concentration of 0.97 μg/ml. This step is performed in a biological safety cabinet.
9. Once sealed the tube is mixed in vortex for 10 seconds. Obtaining Gel: The mixture is formulated (Solution+g)
10. Add 0.85 g of Hydroxyethylcellulose to the prepared mixture.
11. Mix gently until homogeneous.
12. The preparation is isolated from light using aluminum foil, and then stored at 4-25° C. and covered. It should be left to rest between 6 and 8 hours until the bubbles are eliminated.

Example 23

Gel composition of the Invention. Preparation of the Mixture No. 13 (M13) in the Laboratory The composition of the invention comprises:
a. 3.00 mg/mL Polysorbate 80
b. 1 mg/mL ascorbic acid
c. 6.50 mg/mL lactic acid (85%-90% purity)
d. 0.50 mg/mL EDTA
e. 3.00 mg/mL ethosuximide
f. 0.97 μg/mL DNase
g. 17 mg/mL Hydroxyethyl Cellulose Solution: The mixture is formulated (a+b+c+d+e+f)

In 50 ml of mixing solvent are added: 50 mg of ascorbic acid, 25 mg of EDTA, 150 mg of ethosuximide, 50 µg of rh-Dornase alfa, 141 µl of Polysorbate 80 and 318 µl of lactic acid.

Preparation Mode 1. 50 mg of ascorbic acid and 25 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.
During stirring, 141 µl of Polysorbate 80 is added with 200 µl tips by cutting the tip of it.
4. Next, the volume 318 µl of lactic acid is added to the preparation.
5. The 150 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min.
9. 50 mL of preparation of step 8 is placed in conical tubes (50 ml) and 0.05 mL of Dornase alfa 1 mg/mL enzyme Pulmozyme (Roche, Basel, Switzerland) is added under sterile conditions to achieve a final concentration of 1.00 µg/ml. This step is performed in a biological safety cabinet.
10. Once sealed the tube is mixed in vortex for 10 seconds.
Obtaining Gel: The mixture is formulated (Solution+g)
12. Add 0.85 g of Hydroxyethylcellulose to the prepared mixture.
13. Mix gently until homogeneous.
14. The preparation is isolated from light using aluminum foil, and then stored at 4-25° C. and covered. It should be left to rest between 6 and 8 hours until the bubbles are eliminated.

Example 24

Gel Composition of the Invention Preparation of the Mixture No. 15 (M15) in the Laboratory The composition of the invention is composed of:
a. 2.00 mg/mL Polysorbate 80
b. 0.50 mg/mL ascorbic acid
c. 1.63 mg/mL lactic acid (85%-90% purity)
d. 0.25 mg/mL EDTA
e. 0.50 mg/mL ethosuximide
f. 3.90 µg/mL DNase
g. 17 mg/mL Hydroxyethyl Cellulose Solution: The mixture is formulated (a+b+c+d+e+f)

In 50 ml of mixing solvent are added: 25 mg of ascorbic acid, 12.5 mg of EDTA, 25 mg of ethosuximide, 200 µg of rh-Dornase alfa, 94 µl of Polysorbate 80 and 80 µl of lactic acid.

Preparation Mode 1. 25 mg of ascorbic acid and 12.5 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.
During stirring, 94 µl of Polysorbate 80 is added with 200 µl tips by cutting the tip of it.
4. Next, the volume 80 µl of lactic acid is added to the preparation.
5. The 25 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min
9. 50 mL of preparation of step 8 is placed in conical tubes (50 ml) and 0.20 ml of Dornase alfa 1 mg/mL enzyme Pulmozyme (Roche, Basel, Switzerland) is added under sterile conditions to achieve a final concentration of 3.90 µg/ml. This step is performed in a biological safety cabinet.
10. Once sealed the tube is mixed in vortex for 10 seconds. Obtaining Gel: The mixture is formulated (Solution+g)
11. Add 0.85 g of Hydroxyethylcellulose to the prepared mixture.
12. Mix gently until homogeneous.
13. The preparation is isolated from light using aluminum foil, and then stored at 4-25° C. and covered. It should be left to rest between 6 and 8 hours until the bubbles are eliminated.

Example 25

Gel Composition of the Invention Preparation of the Mixture No. 16 (M16) in the Laboratory The composition of the invention comprises:
a. 3.00 mg/mL Polysorbate 80
b. 2.50 mg/mL ascorbic acid
c. 8.67 mg/mL lactic acid (85%-90% purity)
d. 0.75 mg/mL EDTA
e. 30.00 mg/mL ethosuximide
f. 3.90 µg/mL DNase
g. 17 mg/mL Hydroxyethyl Cellulose Solution: The mixture is formulated (a+b+c+d+e+f)

In 50 ml of mixing solvent are added: 125 mg of ascorbic acid, 37.50 mg of EDTA, 1500 mg of ethosuximide, 200 µg of rh-Dornase alfa, 141 µl of Polysorbate 80 and 424 µl of lactic acid.

Preparation Mode 1. 125 mg of ascorbic acid and 37.50 mg of EDTA are weighed on watch glass with analytical balance Radwag AS 220 R2 (Radwag LLC, Radom, Poland).
2. With the help of the mixing solvent, this substance is eluted on a glass beaker so as not to leave any particles in the watch glass.
3. After adding the rest of the 50 ml of the solvent mixture into the beaker, the preparation is placed on a NUMAK GL-3250A magnetic stirrer (Numak Technology LLC, Dubai, UAE) for 5 min until the solid particles have partially dissolved.

During stirring, 141 µl of Polysorbate 80 is added with 200 µl tips by cutting the tip of it.

4. Next, the volume 424 µl of lactic acid is added to the preparation.
5. The 1500 mg of ethosuximide are added.
6. Once these substances are added, the mixture is left stirring for an extra 5 minutes.
7. The solution is brought to a final pH of 5.5, placing 50 mL of solution with a calibrated pH meter Lutron PH-206 in a 100 mL beaker on a stirrer at low revolutions and adding the alkaline solution dropwise until pH level is reached being careful with the effervescence generated by its aggregate.
8. The preparation is sterilized in autoclave Arcano LS-B75L at 120° C. at 1 atm overpressure for 10 min.
9. 50 mL of preparation of step 8 is placed in conical tubes (50 ml) and 0.20 ml of Dornase alfa 1 mg/mL enzyme Pulmozyme (Roche, Basel, Switzerland) is added under sterile conditions to achieve a final concentration of 3.90 µg/mL. This step is performed in a biological safety cabinet.
10. Once sealed the tube is mixed in vortex for 10 seconds. Obtaining Gel: The mixture is formulated (Solution+g)
11. Add 0.85 g of Hydroxyethylcellulose to the prepared mixture.
12. Mix gently until homogeneous.
13. The preparation is isolated from light using aluminum foil, and then stored at 4-25° C. and covered. It should be left to rest between 6 and 8 hours until the bubbles are eliminated.

Examples related to tests with the compositions of the present invention

Various compositions of the present invention have been formulated and have been tested to demonstrate their technical effects.

A summary of some compositions of the invention used to evaluate the present invention can be seen in the following table:

TABLE 1

Concentrations of the different components in mixing solvent (MS; pH 5.5) from the tested compositions

|  | LA (mg/mL) | PS80 (mg/mL) | EDTA (mg/mL) | AA (mg/mL) | Etho (mg/mL) | rh-dornase alfa (µg/mL) |
|---|---|---|---|---|---|---|
| M0 | 6.50 | 0 | 0 | 0 | 3.0 | 0.97 |
| M13 | 6.50 | 3.0 | 0.50 | 1.0 | 3.0 | 0.97 |
| M15 | 1.63 | 2.00 | 0.25 | 0.50 | 0.50 | 3.90 |
| M16 | 8.67 | 3.00 | 0.75 | 2.50 | 30.00 | 3.90 |

Solutions of individual molecules were also tested (prepared as it can be seen in example 1) to demonstrate synergistic properties of the composition of the present invention. The tested solutions were:
1. Lactic acid (LA) in Mixing solvent: 1.63 mg/mL, 6.50 mg/mL, 8.67 mg/mL. Final pH of all solutions: 5.5
2. Polysorbate 80 (PS80) in Mixing solvent: 2.0 mg/mL, 3.0 mg/mL. Final pH of all solutions: 5.5
3. EDTA in Mixing solvent: 0.25 mg/mL, 0.50 mg/mL, 0.75 mg/mL Final pH of all solutions: 5.5
4. Ascorbic acid (AA) in Mixing solvent: 0.5 mg/mL, 1.0 mg/mL, 2.5 mg/mL. Final pH of all solutions: 5.5
5. Ethosuximide (Etho) in Mixing solvent: 0.50 mg/mL, 3.00 mg/mL, 30.00 mg/mL. Final pH of all solutions: 5.5
6. Dornase alfa (D1) in Mixing solvent: 250 µg/mL, 125 µg/mL, 62.5 µg/mL, 31.2 µg/mL, 15.6 µg/mL, 7.8 µg/mL, 3.9 µg/mL, 1.9 µg/mL, 0.97 µg/mL, 0.5 µg/mL. Final pH of all solutions: 5.5.

Example 26

Antipathogenic Effects

Bacteria Strains

1) Mucoid *Pseudomonas aeruginosa* (Internal Code LEF037): Clinical isolation from chronic venous ulcer with more than 6 months of evolution.
2) Methicillin resistant *Staphylococcus aureus* (Internal Code LEF006). Clinical isolation from a chronic venous leg ulcer with more than 6 months of evolution.

Bacterial suspensions: *P. aeruginosa* LEF037 was grown for 12 h in Luria-Bertani (LB) culture medium at 37° C. From this culture, a suspension ($OD_{600\ nm}$=0.120) was prepared in LB. *S. aureus* LEF006 was grown for 12 h in Brain Heart Infusion (BHI) culture medium at 37° C. From this culture, a suspension ($OD_{600\ nm}$=0.120) was prepared in BHI.

Controls: In the performed assays it has been used the the following controls:
a. Normal growth control for *P. aeruginosa*: Luria Bertani medium (LB) (pH 7.2)
b. Normal growth control for *S. aureus*: Brain Heart Infusion (BHI) medium (pH 7.2)
c. Dilution effect control: Mixing solvent (MS) (pH 5.50).
d. Control of newly obtained LAPS effect: LAPS stored for 24 hours at 4° C. (pH 5.22) (LAPS 24 h).
e. LAPS activity conservation control: LAPS stored for 6 months at 4° C. (pH 6.05) (LAPS6m).

*Lactobacillus plantarum* supernatant (LAPS): LAPS controls were prepared according to example 1 details. *L. plantarum* ATCC 10241 was grown for 12 h in de Man Rogosa Sharpe (MRS) (Britania. Argentina) at 37° C. Supernatant (LAPS) was obtained by centrifugation for 15 min at 8000 rpm and filtration with Millipore filters of 0.22 µm. This supernatant corresponds to the patent application No. AR093779 and is taken as the known product of the best therapeutic effect for chronic wounds treatment. This product presents some problems that the present invention intends to solve. On the one hand, it is observed from the tests presented below that it loses its efficiency over time. It also presents regulatory problems because it does not have an absolutely defined composition because it depends on a fermentation process. The present invention achieves great stability extended over time and is constituted from components absolutely defined and approved for human therapeutic use.

Solutions of individual molecules: All solutions were prepared in mixing solvent with a final pH of 5.5 according to example 1. The prepared solutions were: 1. Lactic acid (LA) (1.63, 6.50 and 8.67 mg/mL); 2. Polysorbate 80 (PS80) (2.0 and 3.0 mg/mL); 3. EDTA (0.25, 0.50 and 0.75 mg/mL); 4. Ascorbic acid (AA) (0.5, 1.0 and 2.5 mg/mL); 5. Ethosuximide (Etho) (0.50, 3.00 and 30.00 mg/mL); 6. rh-Dornase alfa (D1) (0.97 and 3.9 µg/mL).

M0, M13, M15 and M16 (see Table 1). Compositions of the invention were elaborated according to the examples 18 to 21.

Tests for the determination of the bacteriostatic effect: For the bacteriostatic assays, 96-well plates (Deltalab. Argentina) (200 µL capacity) were used. All assays were performed in triplicate using 100 µL of LB culture medium or BHI culture media with 50 µL of the bacterial suspension of *P. aeruginosa* or *S. aureus*, respectively. Then, the following samples were placed:
a. 50 µL of the controls (See controls),
b. 50 µL solutions of individual molecules (See Solutions of individual molecules)
c. 50 µL mixtures of molecules.

Subsequently, the microplate was placed in a microplate reader (Multiskan Go. Thermo Scientific. Germany) using the following reading program: a) Incubation at 37° C.; b) Slight agitation (3 seconds duration) every 58 minutes, c) Absorbance reading cycle at 600 nm once per hour for 24 h. The initial optical density (OD) for all wells was 0.100. Data was analyzed in Microsoft Excel®, calculating averages. The results are shown in column as a percentage of bacteriostatic effect at 24 h.

Tests for the determination of the bactericidal effect: From rom the tests used for the determination of the bacteriostatic effect, 10 µL aliquots were taken from each well, serial dilutions were made and one aliquot of each dilution was seeded on LB or BHI agar according to the bacterial strain. Initial numbers of Colony-forming units (CFU) were counted to compare to the final number of CFU obtained after 24 h of treatment. The number of surviving bacteria was calculated, representing them in columns according to the number CFU/mL obtained after the treatment.

Tests for the determination of the biofilm inhibition effect: After 24 h of the growth inhibition test, the contents of the wells were discarded, and the empty wells were washed three times with sterile saline solution. The plates were dried at room temperature for 15 minutes (face down, on absorbent paper). To each well, 200 µL of 0.1% violet crystal was added and the plate was incubated for 15 min at room temperature with gentle and constant stirring in Vortex (Labnet) to stain the biofilm adhered to the wells wall. After that, the contents of the wells were discarded, washed three times with sterile saline solution and dried at room temperature for 15 minutes (face down, on absorbent paper). Subsequently, to dissolve crystal violet adhered to the biofilm, 200 µL of 96° ethanol was added to each well and the plates were incubated for 10 minutes with gentle and constant stirring in Vortex (Labnet) at room temperature. The amount of crystal violet is directly proportional to the amount of biofilm formed. In this manner, in each well a solution was obtained, whose intensity color is directly proportional to the amount of biofilm formed. Absorbance reading was done accurately at 540 nm, at 37° C. in the Multiskan Go microplate reader (Thermo Scientific). Data were processed in Microsoft Excel®, averages were calculated, and the results are shown in column as a percentage of inhibition of biofilm formation.

Tests for the determination of the biofilm disruption effect: In 96-well plates (Deltalab) it was placed 150 µL of culture medium+50 µL of bacterial suspension. The plates were incubated in a humid chamber, at 37° C. for 24 hours until biofilm formation. After that, the contents of the wells were carefully discarded, washed gently three times with sterile saline solution, avoiding the loss of biofilm adhered to the walls. The plates were dried for 20 min at room temperature in a biological safety cabinet. Subsequently, 150 µL of culture medium was added and respectively: 50 µL of controls, 50 µL solutions of individual molecules and 50 µL mixtures of molecules. All trials were performed in triplicate. The plates were incubated in a humid chamber at 37° C. for 24 hours. After that, the contents of the wells were discarded and washed three times with sterile saline. The plates were dried at room temperature for 15 minutes (face down on absorbent paper). The wells were stained with 200 µL/well of 0.1% violet crystal, for 15 minutes with gentle and constant stirring in Vortex (Labnet) at room temperature. The contents of the wells were discarded, washed three times with sterile saline and the plates were dried at room temperature for 15 minutes (face down on absorbent paper). Finally, 200 µL/well of 96° ethanol was added to dissolve Violet Crystal attached to biofilm. Plates were incubated for 10 minutes with gentle and constant stirring in Vortex (Labnet) at room temperature. The absorbance of the resulting solutions was measured in the Multiskan Go microplate reader (Thermo Scientific) at 540 nm (37° C.). Data was processed in Microsoft Excel®, averages were calculated, and the results are shown in column as a percentage of biofilm disruption.

Results and Discussions

Figure 2:
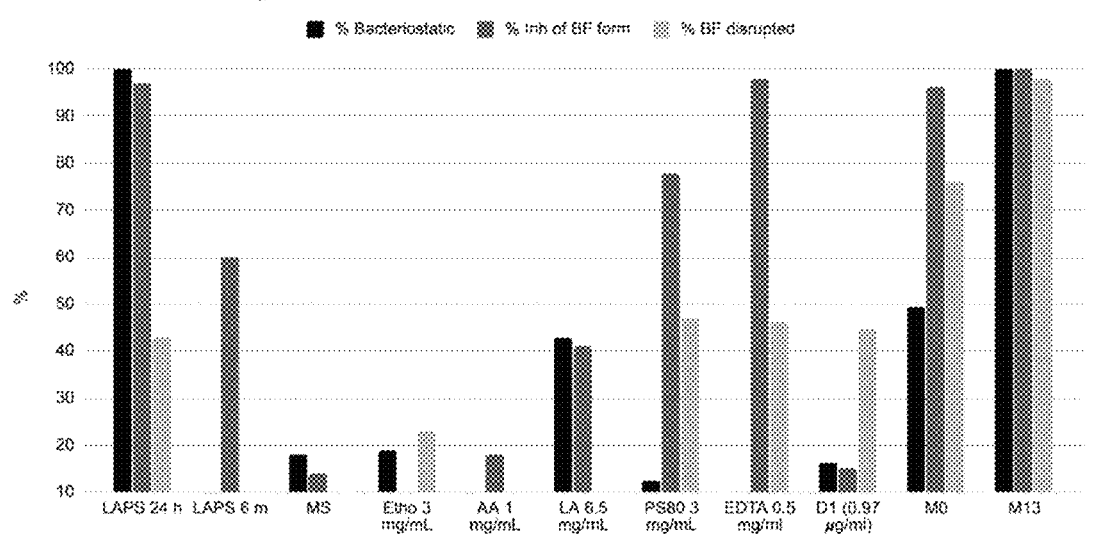
FIG. 2: Percentages of the antipathogenic properties studied on *P. aeruginosa*: bacteriostatic activity, inhibition of the Biofilm (BF) formation and preformed biofilm disruption caused by compositions M0 and M13 and the individual molecules at the concentrations that there are in the mentioned compositions. Etho=Ethosuximide; AA=Ascorbic Acid; LA=Lactic Acid; PS80=Polysorbate 80; D1=DNAse 1; MS=Mixing solvent; LAPS=*Lactobacillus plantarum* Supernatant; M=Mixture

FIGS. 2 shows the percentages of different antipathogenic effects: the bacteriostatic activity, inhibition of the Biofilm (BF) formation and preformed biofilm disruption over *Pseudomonas aeruginosa* caused by composition M0 and M13 and the individual molecules at the concentrations that there are in the mentioned compositions. The figure also shows these properties for LAPS 24 hours, LAPS 6 months and mixing solvent (MS).

The individual molecules presented some activity for each property. Nevertheless, MO and M13 show a synergic power for all the activities. Although LAPS 24 h had a great bacteriostatic and inhibition BF effects, its disruption effect over biofilm was lower than compositions. In addition, after 6 months LAPS lost their anti-pathogenic effects drastically.

Figure 3:
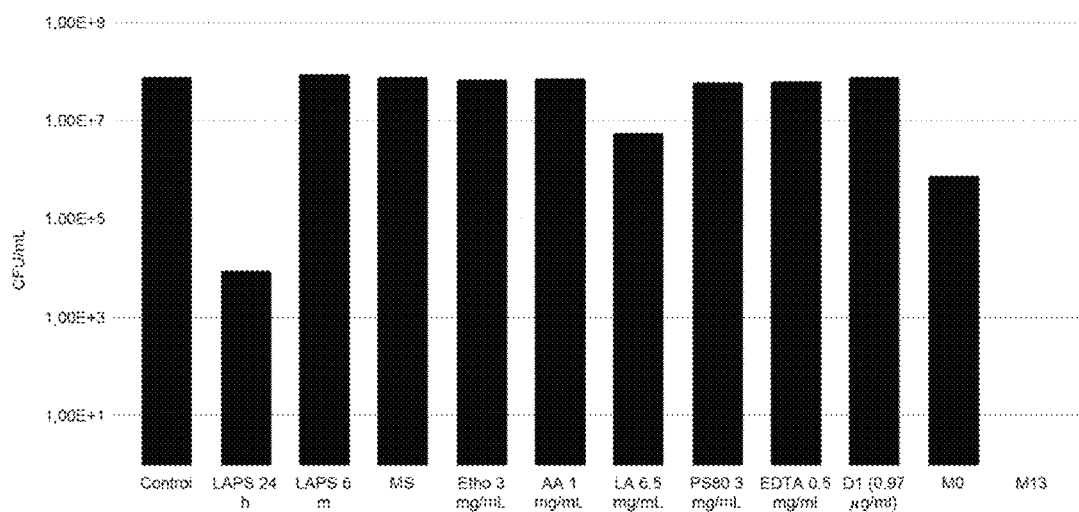
FIG. 3: Bactericidal effect expressed in the surviving bacteria (CFU/mL) of *Pseudomonas aeruginosa* after 24 h of treatment using compositions M0 and M13 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent

FIG. 3 shows the bactericidal effect expressed in the surviving bacteria (CFU/mL) of *Pseudomonas aeruginosa* after 24 h of treatment using compositions M0 and M13 and the different individual molecules at concentrations that are in the mentioned compositions.

As FIG. 3 shows, no one of the individual molecules caused a bactericide effect because the survival bacteria level was similar to the control (non-treated). LAPS showed an important bactericide effect, but it is lost with the time. M0 shows a remarkable bactericide effect while M13 caused an absolute elimination of the bacteria.

Figure 4:
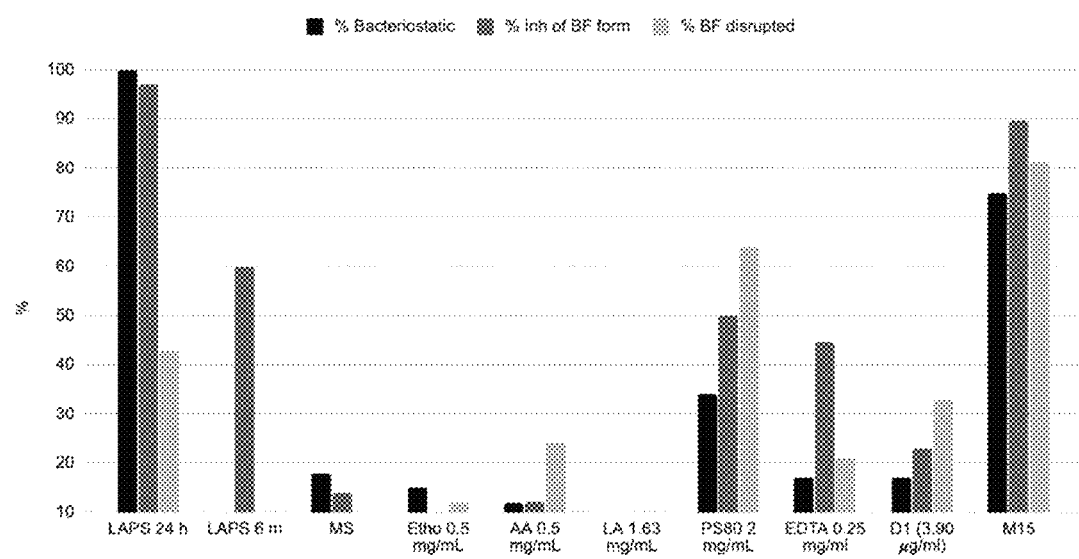
FIG. 4: Percentages of different antipathogenic effects: the bacteriostatic activity, inhibition of the Biofilm (BF) formation and preformed biofilm disruption over *Pseudomonas aeruginosa* caused by composition M15 and the individual molecules at the concentrations that there are in the mentioned composition. Etho=Ethosuximide; AA=Ascorbic Acid; LA=Lactic Acid; PS80=Polysorbate80; D1=DNAse 1; LAPS=*Lactobacillus plantarum* Supernatant; M=Mixture; MS=Mixing solvent

FIG. 4 shows the percentages of different antipathogenic effects: the bacteriostatic activity, inhibition of the Biofilm (BF) formation and preformed biofilm disruption over *Pseudomonas aeruginosa* caused by composition M15 and the individual molecules at the concentrations that there are in the mentioned compositions. The figure also shows these properties for LAPS 24 hours, LAPS 6 months and mixing solvent (MS). The individual molecules presented some activity for each property. Nevertheless, M15 shows a synergic power for all the activities. Although LAPS 24 h had a great bacteriostatic and inhibition BF effects, its disruption effect over biofilm was lower than the composition M15. In addition, after 6 months LAPS lost their antipathogenic effects drastically.

Figure 5:
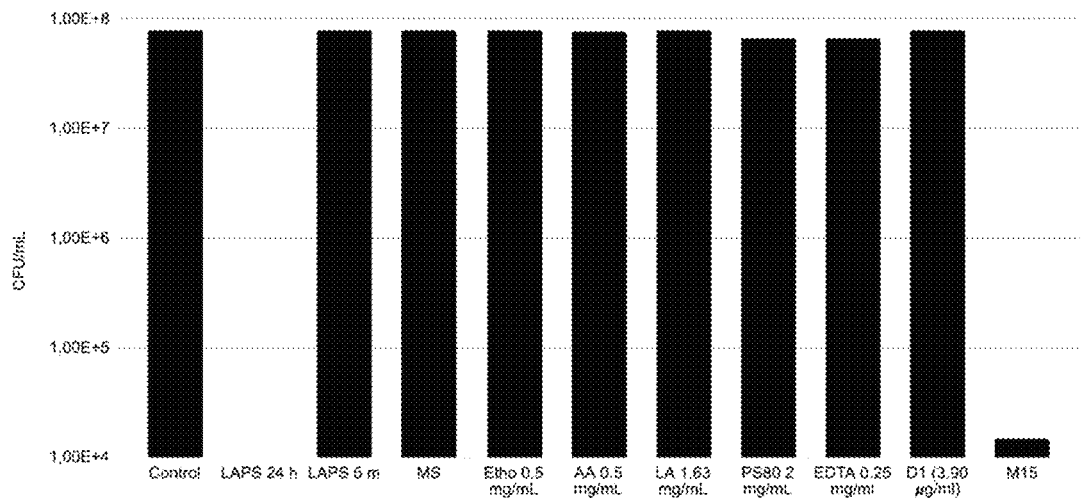
FIG. 5: Bactericidal effect expressed in the surviving bacteria (CFU/mL) of *Pseudomonas aeruginosa* after 24 h of treatment using composition M15 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent

FIG. 5 shows the bactericidal effect expressed in the surviving bacteria (CFU/mL) of *Pseudomonas aeruginosa* after 24 h of treatment using the composition M15 and the different individual molecules at concentrations that are in the mentioned composition. As the figure shows, no one of the individual molecules caused a bactericide effect because the survival bacteria level was similar to the control (non-treated). LAPS had an important bactericide effect but it is lost with the time. M15 caused a great elimination of the bacteria.

Figure 6:
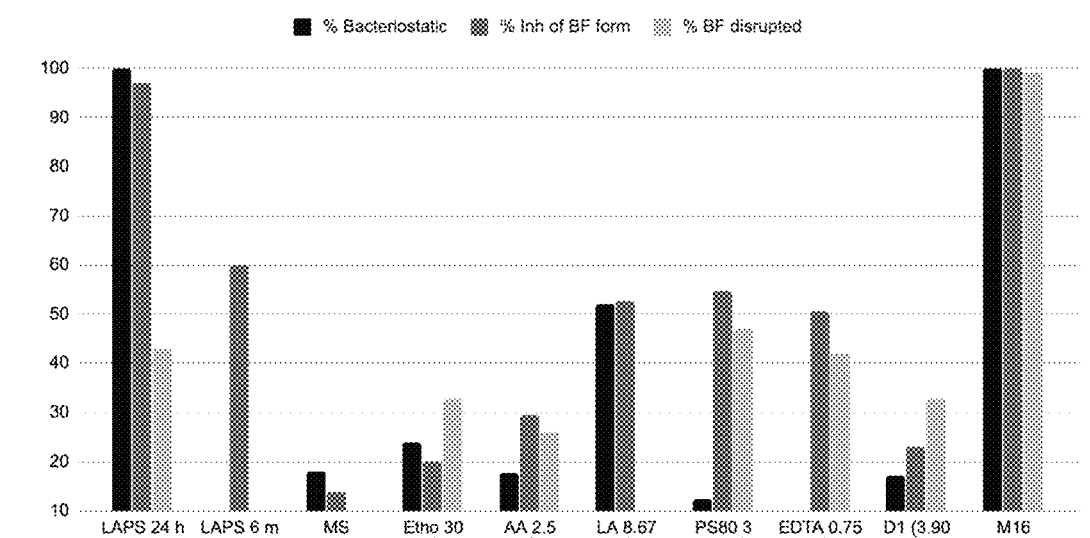
FIG. 6: Percentages of different antipathogenic effects: the bacteriostatic activity, inhibition of the Biofilm (BF) formation and preformed biofilm disruption over *Pseudomonas aeruginosa* caused by composition M16 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent.

FIG. 6 shows the percentages of different antipathogenic effects: the bacteriostatic activity, inhibition of the Biofilm (BF) formation and preformed biofilm disruption over *Pseudomonas aeruginosa* caused by the composition M16 and the individual molecules at the concentrations that there are in the mentioned composition. The figure also shows these properties for 24 hours LAPS, 6 months LAPS and mixing solvent (MS). The individual molecules presented some activity for each property. Nevertheless, M16 shows a remarkable synergic power for all the activities. Although LAPS 24 h had a great bacteriostatic and inhibition BF effects, its disruption effect over biofilm was lower than formulation. In addition, after 6 months LAPS lost their anti-pathogenic effects drastically.

Figure 7:
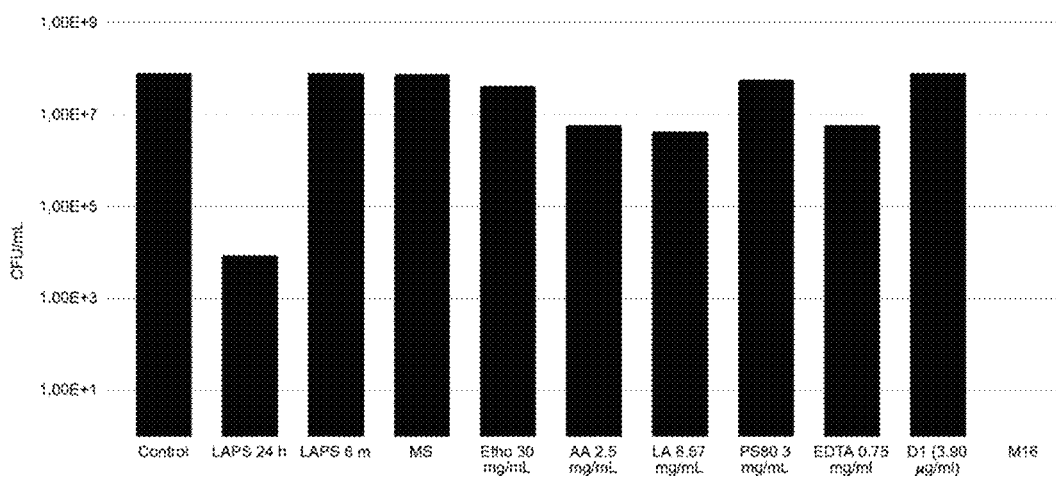
FIG. 7: Bactericidal effect expressed in the surviving bacteria (CFU/mL) of *Pseudomonas aeruginosa* after 24 h of treatment using composition M16 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent.

FIG. 7 shows the bactericidal effect expressed in the surviving bacteria (CFU/mL) of *Pseudomonas aeruginosa* after 24 h of treatment using the composition M16 and the different individual molecules at concentrations that are in the mentioned composition. As the figure shows, some of the individual molecules caused a low bactericide effect because the survival bacteria level was similar to the control (non-treated). LAPS had an important bactericide effect, but it is lost with the time, while M16 caused a complete elimination of the bacteria.

Figure 8:
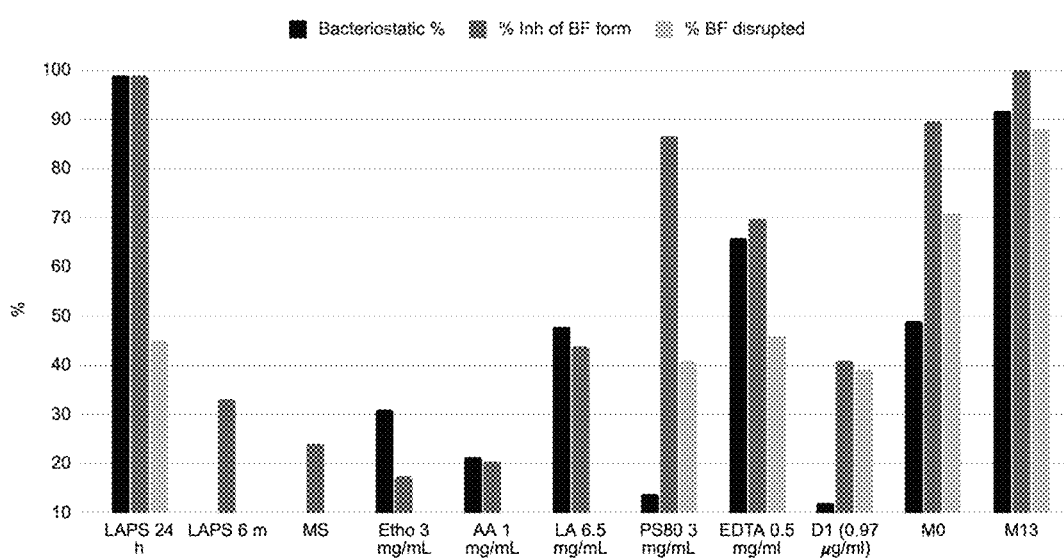
FIG. 8: Percentages of the antipathogenic properties studied on *S. aureus*: bacteriostatic activity, inhibition of the Biofilm (BF) formation and preformed biofilm disruption caused by composition M0 and M13 and the individual molecules at the concentrations that there are in the mentioned compositions. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent.

FIG. 8 shows the percentages of different antipathogenic effects: the bacteriostatic activity, inhibition of the Biofilm (BF) formation and preformed biofilm disruption over *Staphylococcus aureus* caused by compositions M0 and M13 and the individual molecules at the concentrations that there are in the mentioned compositions. The figure also shows these properties for 24 hours, 6 months LAPS and mixing solvent (MS).

The individual molecules presented some activity for each property. Nevertheless, M13 shows a synergic power for all the activities. M0 presented synergism for the inhibition of the Biofilm (BF) formation and performed biofilm disruption. Although LAPS 24 h had a great bacteriostatic and inhibition BF effects, its disruption effect over biofilm was lower than formulations. In addition, after 6 months LAPS lost their anti-pathogenic effects drastically.

Figure 9:
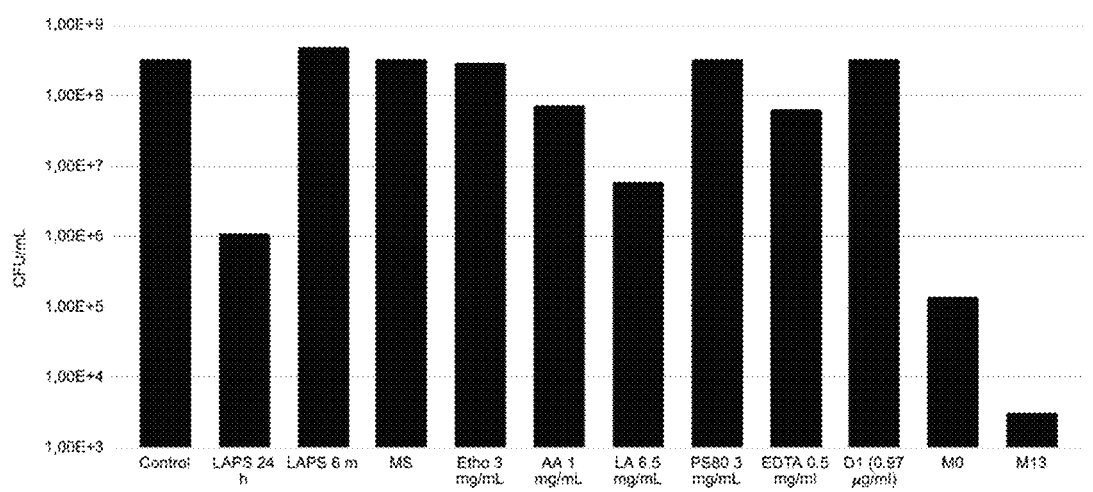
FIG. 9: Bactericidal effect expressed in the surviving bacteria (CFU/mL) of *S. aureus* after 24 h of treatment using compositions M0 and M13 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent.

FIG. 9 shows the bactericidal effect expressed in the surviving bacteria (CFU/mL) of *Staphylococcus aureus* after 24 h of treatment using compositions M0 and M13 and the different individual molecules at concentrations that are in the mentioned compositions.

As the figure shows, the most of the individual molecules did not cause a bactericide effect because the survival bacteria level was similar to the control (non-treated). LAPS had an important bactericide effect, but it is lost with the time. M0 shows a remarkable bactericide effect while the bacteria elimination by M13 was higher.

Figure 10:
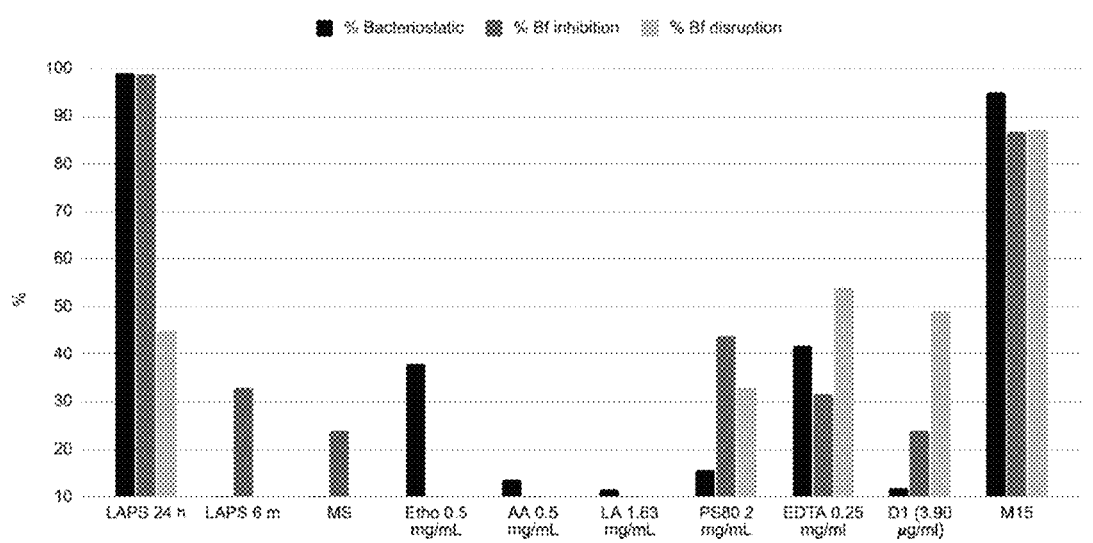
FIG. 10: Percentages of different antipathogenic effects: the bacteriostatic activity, inhibition of the Biofilm (BF) formation and preformed biofilm disruption over *S. aureus* caused by composition M15 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent

FIG. 10 shows the percentages of different antipathogenic effects: the bacteriostatic activity, inhibition of the Biofilm (BF) formation and preformed biofilm disruption over *S. aureus* caused by composition M15 and the individual molecules at the concentrations that there are in the mentioned composition. The figure also shows these properties for 24 hours, 6 months LAPS and mixing solvent (MS).

The individual molecules presented some activity for each property. Nevertheless, M15 shows a synergic power for all the activities. Although LAPS 24 h had a great bacteriostatic and inhibition BF effects, its disruption effect over biofilm was lower than the formulation. In addition, after 6 months LAPS lost their anti-pathogenic effects drastically.

Figure 11:
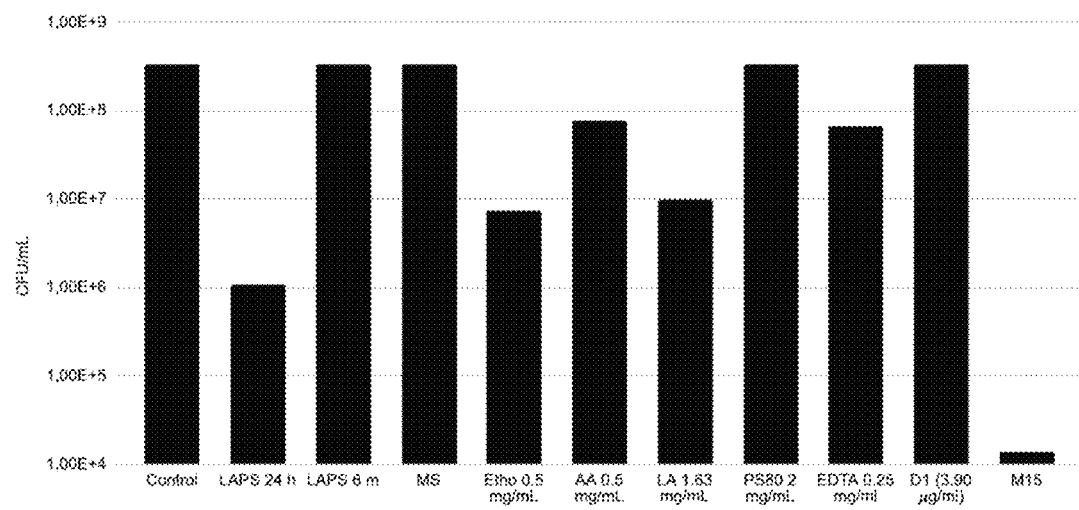
FIG. 11: Bactericidal effect expressed in the surviving bacteria (CFU/mL) of *S. aureus* after 24 h of treatment using composition M15 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent.

FIG. 11 shows the bactericidal effect expressed in the surviving bacteria (CFU/mL) of *Staphylococcus aureus* after 24 h of treatment using the composition M15 and the different individual molecules at concentrations that are in the mentioned composition.

As the figure shows, the most of individual molecules did not cause a bactericide effect because the survival bacteria level was similar to the control (non-treated). LAPS had some bactericide effect, but it is lost with the time. Finally, M15 caused a great elimination of the bacteria.

Figure 12:
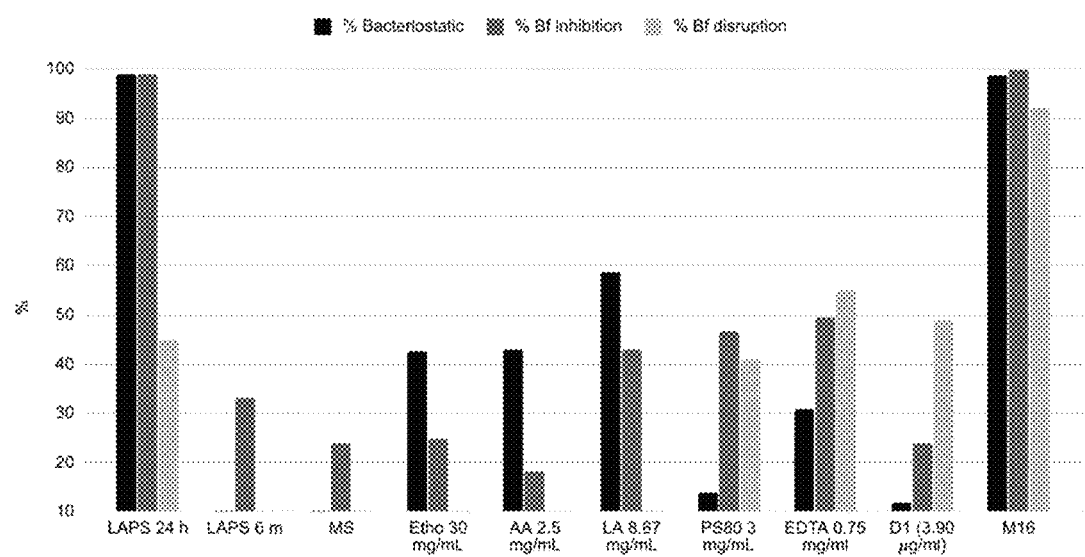
FIG. 12: Percentages of different antipathogenic effects: the bacteriostatic activity, inhibition of the Biofilm (BF) formation and preformed biofilm disruption over *S. aureus* caused by composition M16 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent.

FIG. 12 shows the percentages of different antipathogenic effects: the bacteriostatic activity, inhibition of the Biofilm (BF) formation and preformed biofilm disruption over *Staphylococcus aureus* caused by the composition M16 and the individual molecules at the concentrations that there are in the mentioned formulation. The figure also shows these properties for 24 hours, 6 months LAPS and mixing solvent (MS).

The individual molecules presented some activity for each property. Nevertheless, M16 shows a remarkable synergic power for all the activities. Although LAPS 24 h had a great bacteriostatic and inhibition BF effects, its disruption effect over biofilm was lower than formulation. In addition, after 6 months LAPS lost their anti-pathogenic effects drastically.

Figure 13:
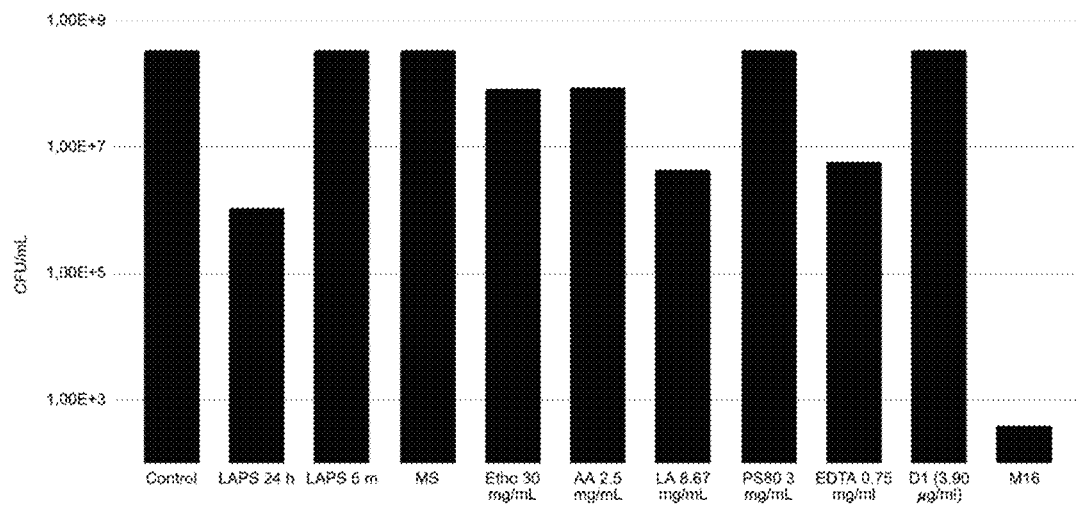
FIG. 13: Bactericidal effect expressed in the surviving bacteria (CFU/mL) of *S. aureus* after 24 h of treatment using composition M16 and the individual molecules at the concentrations that there are in the mentioned composition. Etho=Ethosuximide; AA=Ascorbic Acid; LA=Lactic Acid; PS80=Polysorbate 80; D1=DNAse 1; LAPS=*Lactobacillus plantarum* Supernatant; M=Mixture; MS=Mixing solvent.

FIG. 13 shows the bactericidal effect expressed in the surviving bacteria (CFU/mL) of *Staphylococcus aureus* after 24 h of treatment using the composition M16 and the different individual molecules at concentrations that are in the mentioned composition.

As FIG. 13 shows, some of the individual molecules cause a low bactericide effect because the survival bacteria level was similar to the control (non-treated). LAPS had an important bactericide effect, but it was lost with the time, while M16 caused the biggest elimination of the bacteria.

The biofilm disruption capacity is one of the most sought-after properties in chronic wound treatment, since the patient goes to the doctor when the biofilm has already formed on the wound. It is known that conventional antimicrobials are not capable of causing biofilm disruption, having a relative efficacy especially in vivo, due to:

a. Each species has a different chemical composition in the matrix of its biofilm.
b. Infections are polymicrobial which leads to the formation of mixed biofilms.
c. Existing treatments point to a particular chemical composition.

That is why existing treatments always leave mixed biofilm remains that become new sources of infection, chronifying the infection. Good disruptive treatments should attack mixed biofilms and biofilms of different species, producing disruptions close to 100%.

Conclusion

Surprisingly, the components of this invention show synergistic bacteriostatic, bactericidal, biofilm inhibition and disruption properties in the most commonly identified bacteria in chronic wounds (*P. aeruginosa* and *S. aureus*). This invention also shows superior effect to LAPS in the properties studied on *P. aeruginosa* and *S. aureus*.

Example 27

Antioxidant Capacity of the Compositions of Invention

The method to determine the antioxidant activity is based on the 2,2-diphenyl-1-picryl hydrazyl (DPPH) capacity for catching free radicals (a proton-give substance is an antioxidant substance). DPPH* radical accepts a proton from the antioxidant substance and becomes in DPPH. In this way, the antioxidant effect is proportional to the DPPH* decrease. DPPH* has its absorbance maximum at 517 nm, changing from purple to yellow when DPPH is forming. Therefore, the antioxidant effect could be measured following the absorbance fall at 517 nm by spectrophotometry. Then, with the initial and final values of absorbance of the samples, Inhibition Coefficient 50 (IC50) is calculated. IC50 represents the minimum concentration of the antioxidant substance needed to reduce the 50% of the DPPH*. To obtain the IC50, two increasing concentration curves were performed: the first using the tested sample and the second using a reference standard (Trolox). Finally, percentage of the relative antioxidant activity (% AAR) is calculated following recommendations from Sharma et al. (42)

Preparation of the stock solution (SS) and the working solution (WS) of the DPPH* radical: A solution of approximately 100 ppm of DPPH in absolute methanol is prepared. The solution must be reposed at room temperature in the dark for at least 30 minutes. The WS is then prepared from the SS with absolute methanol, until an absorbance of 0.800±0.100 is obtained on the microplate, at a wavelength of 517 nm.

Preparation of the standard Trolox solution: Prepare a SS=500 ppm. To obtain a volume of 10 mL, 5 mg of Trolox should be dissolved in 10 mL of absolute methanol. Six WSs were prepared with concentrations of: 25, 50, 100, 150, 200 and 250 ppm.

Samples: 1) Mixing Solvent (MS), 2) Solutions containing respectively 0.5 and 2.5 mg/mL of ascorbic acid in mixing solvent were prepared as indicated in example 1; 3) M15 (composition of the invention elaborated according to example 20); 4) M16 (composition of the invention elaborated according to example 21); and 5) LAPS (Prepared according to example 1 details).

Spectrophotometry: Absorbance (Abs) readings were performed for triplicate with a spectrophotometer at 517 nm using UV-Vis suitable microplates.
a. Place on the wells: Sample blank (12.5 µL of sample or WS 25 ppm); Samples (12.5 µL of sample or WS from 25 to 250 ppm); Initial DPPH value (12.5 µL of absolute methanol)
b. Reach the zero absorbance with absolute methanol.
c. Add 250 µL of absolute methanol to the sample blank wells.
d. Add 250 µL of DPPH* WS to DPPH baseline and sample wells.
e. Record the absorbance at 517 nm (Initial DPPH Abs)
f. Keep in repose for 30 minutes (in the dark and at room temperature).
g. Record the absorbance at 517 nm (final DPPH Abs).
h. Record the absorbance readings (Blank Abs of samples)
i. Calculate the catching percentage for the samples and Trolox.

Curves with reference standard (Trolox) and with the analyzed sample: Two curves are elaborated, plotting on the ordinate axis (y) the catching % and on the abscissa axis (x), natural logarithm (Ln) of the concentration of Trolox or analyzed sample (ppm of TEAC or sample, respectively). Substitute in each graph the (y) axis with the value 50 and calculate the IC50 using the equation obtained by linear regression of the graph. Then, the % AAR is calculated using the respective IC50 values.

Results

Figure 14:
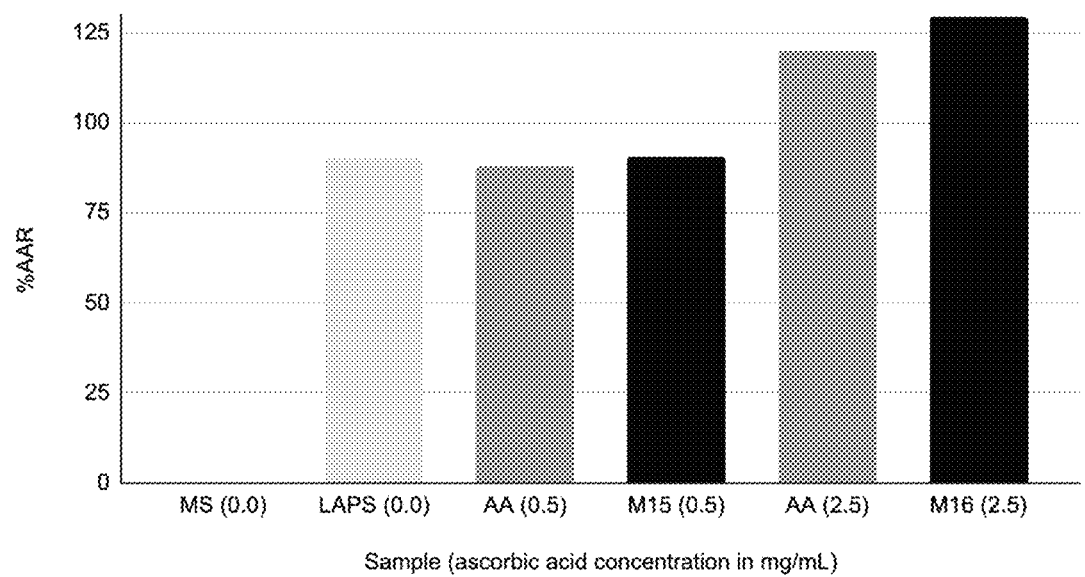
FIG. 14: Percentage of the antioxidant activity relative to Trolox (% AAR) shown by MS, LAPS, AA (0.5 mg/mL and 2.5 mg/mL), M15 and M16. MS=Mixing Solvent; AA=ascorbic acid; LAPS=*Lactobacillus plantarum* Supernatant; M=mixtures

In FIG. 14 could be seen that the mixing solvent did not present antioxidant activity. Although LAPS do not have ascorbic acid, it showed values for % AAR due to its content of phenolic compounds. Surprisingly, compositions M15 and M16 had better antioxidant activity than their equivalent ascorbic acid concentration solutions (AA 0.5 and 2.5 mg/mL).

Conclusion

Compositions of invention enhance the antioxidant properties of ascorbic acid.

Example 28

Chelating Capacity of the Compositions

The following solutions were prepared in Mixing solvent (MS) at pH 7.0. All solutions were supplemented with $ZnCl_2$ (1 ppm), $CaCl_2$ (100 ppm) and $MgCl_2$ (25 ppm). The concentrations of Zn, Ca and Mg used here, were close to those typically found in exudates from chronic wounds. The pH chosen for the reaction (7.0) would result from the combination of compositions of present invention (pH 5.5) and the exudate from a chronic wound (pH 8.5). Prepared solutions were: EDTA (0.25, 0.50 and 0.75 mg/mL) as indicated in example 1; M0, M13, M15 and M16 were elaborated according to examples 18 to 21. and LAPS deproteinized: Over a LAPS 24 h sample obtained according to example 1, a deproteinization process was performed using reagents and indications of the commercial kit employed.

Measurement of remaining Calcium (unchelated) in the prepared solutions: A commercial Calcium measurement kit (Wiener Lab) was used. This is a colorimetric method based on the reaction of calcium with o-cresolphthalein complexone (o-CPC) at alkaline pH, giving a photocolorimetrically measurable magenta complex at 570 nm.

Measurement of remaining Zinc (unchelated) in the prepared solutions: A commercial Zinc measurement kit (Randox Lab) was used. This is a colorimetric method based on the reaction of Zinc with Dimethylglyoxime and Salicylaldoxin at alkaline pH, giving a colored complex photocolorimetrically measurable at 560 nm.

For the determination of Zinc in LAPS, a previous deproteinization step was necessary. Therefore, equal parts of LAPS and deproteinizing reagent (Trichloroacetic Acid 370 mmol/L) were mixed in conical tubes, homogenized and centrifuged for 10 min at 10,000×g. The supernatant was used for the test.

Results

Figure 15:
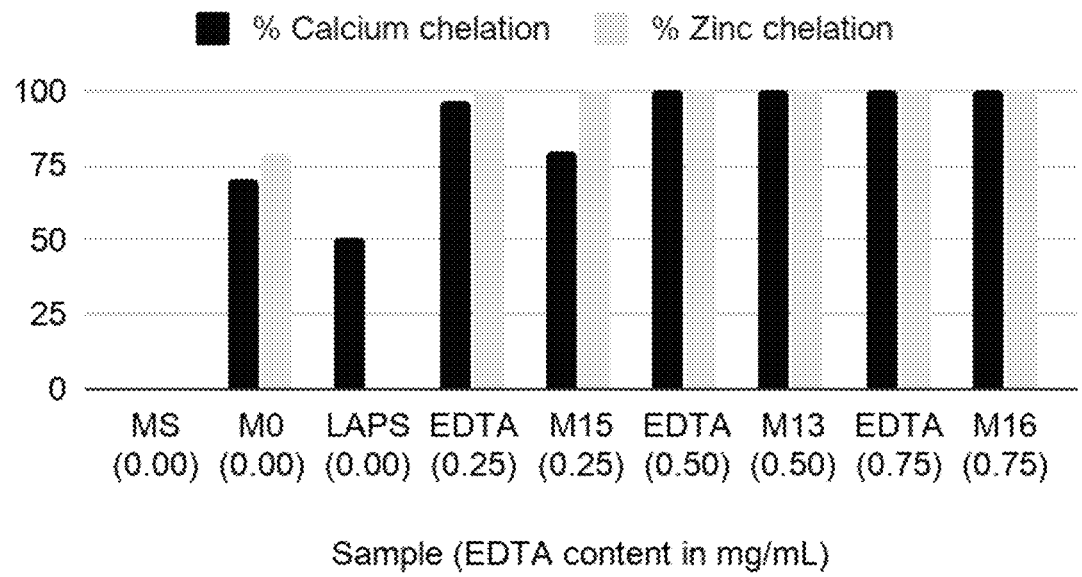
FIG. 15: Calcium and zinc chelation percentage at pH 7.0 showed by mixing solvent (MS), solutions of EDTA in mixing solvent (0.25, 0.50 and 0.75 mg/mL), M0, M13, M15 and M16. MS=Mixing Solving.

FIG. 15 shows that EDTA was able to completely chelate Zinc at all concentrations tested, even when a combination of Zinc, Calcium and Magnesium was used. EDTA was also capable of chelating calcium completely at concentrations of 0.50, 0.75 and 1.00 mg/mL, even when a combination of zinc, calcium and magnesium was used. However, EDTA 0.25 mg/mL was not able to chelate all the available calcium. M0 does not have EDTA, but still showed chelating activity for both calcium and zinc. M15 containing 0.25 mg/mL of EDTA lost calcium chelating power (although not zinc chelating power) compared to its equivalent concentration of EDTA alone. In contrast, M13 and M16 containing 0.50 mg/mL and 0.75 mg/mL of EDTA, respectively, retained the maximum chelating power than their EDTA equivalents alone. All mixtures showed superior chelating capacity compared to LAPS, which also did not have Zinc chelating power.

Conclusion

The compositions have chelating ability independent of EDTA. Surprisingly, the components of the compositions improve the chelating capacity of EDTA.

Example 29

Increasing and Conserving in Time the DNAse Activity From the Compositions

DNAse agar is a culture medium that contains highly polymerized DNA and agar as solidifying agents. The DNA is the substratum of the deoxyribonuclease enzyme (DNAse) which hydrolyzes it. This medium allows to detect DNAse activity in different samples and microorganisms. The presence of the enzyme could be visualized adding hydrochloric acid 1N. The hydrolyzed deoxyribonucleic acid presents transparency while the polymerized deoxyribonucleic acid precipitates generating resulting in a opacity on the culture media Plates preparation: DNAse agar plates were prepared according to manufacturer recommendations (Britania, CABA, Argentina). A volume of 20 mL of the molten media was employed reaching an agar height of 2 mm in the plates. Wells of 5 mm o diameter were made over the agar using a sterile punch. Therefore, the sown volume in each well was $\pi x r^2 \times h = \pi \times (2.5 \text{ mm})^2 \times 2 \text{ mm} = 40 \text{ mm} = 40 \text{ μL}$.

Calibration curve: rh-Dornase Alfa solutions (Roche. Basel, Switzerland) were employed diluted in mixing solvent in the following concentrations: C1 (0.1 μg/mL); C2 (0.97 μg/mL); C3 (2.0 μg/μL); 4 (3.90 μg/mL); C5 (8.0 μg/mL); C6 (10.0 μg/mL); C7 (100.0 μg/mL) y C8 (1000 μg/μL).

Analyzed samples: LAPS, M0, M13, M15, M16 (All gelled with hydroxyethyl cellulose) stored at 25° C. and 4° C. DNAse activity was measured once a week for 6 months. LAPS were prepared as indicated in example 1 and the compositions of the invention were elaborated according to examples 22 to 25.

Seeding on the DNAse agar plates: The points of the calibration curve and the different gelled samples were seeded in duplicate for 6 months.

Incubation: 24 hours at 32° C. (Normal skin temperature in humans)

Revealed: The plates were flooded adding enough HCl (1M) to cover the entire plate's surface. Then, the plates were rested and were observed up to no more than 5 minutes after adding the HCl. DNase activity was measured analyzing the transparent evanescence around the planting zone recording in millimeters the halos diameter.

Results

Figure 16:
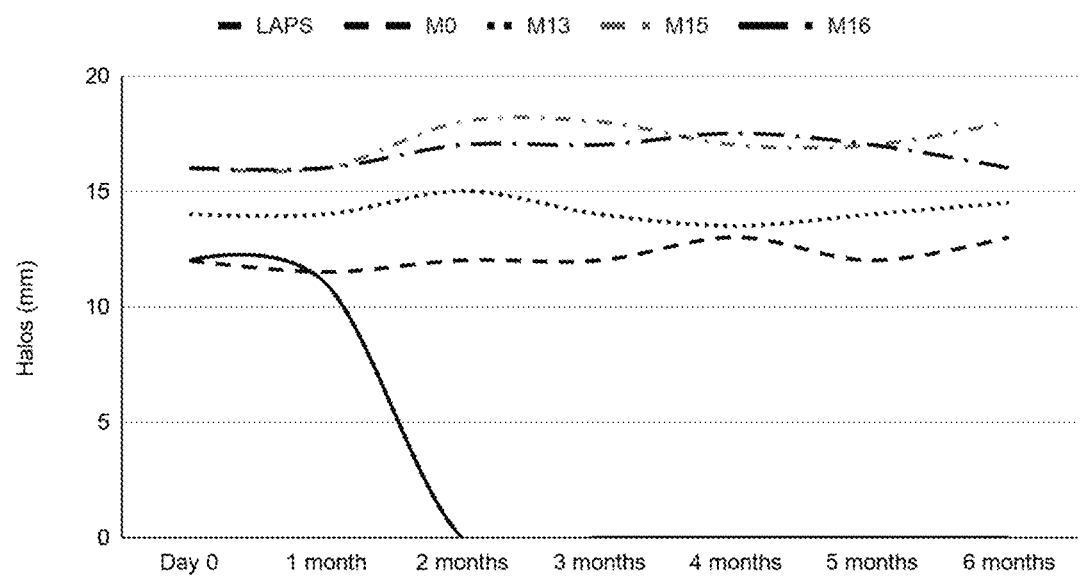
FIG. 16: DNAse activity halos (mm) measured in DNAse agar at different times for the different tested samples to evaluate conservation of enzymatic activity.

The FIG. 16 shows the conservation of the DNAse activity in the invention compositions up to 6 months, while LAPS lost this enzymatic activity in less than 2 months.

Figure 17:
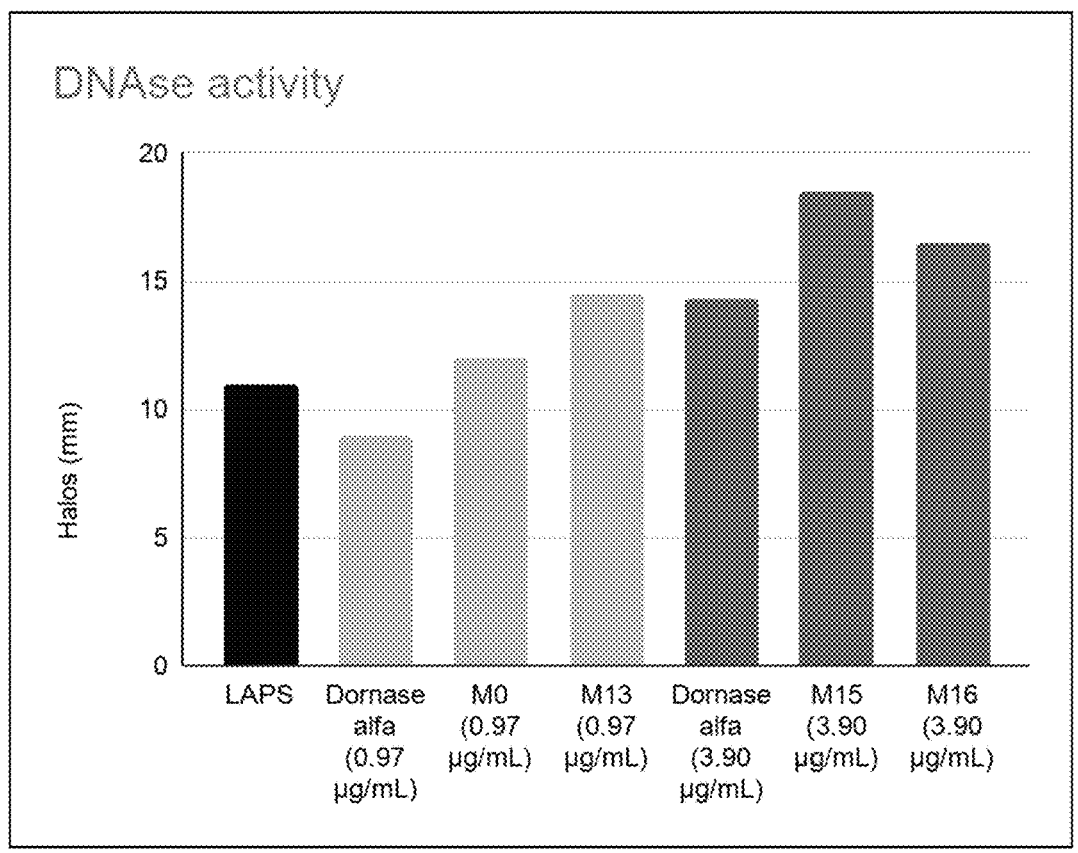
FIG. 17: Halos of DNAse activity of LAPS, Dornase alfa 0.97 μg/mL, M0 and M13 (with 0.97 μg/mL of Dornase alfa each); M15 and M16 (with 3.90 μg/mL of Dornase alfa each) measured in DNAse agar (mm). LAPS=*Lactobacillus plantarum* supernatant; M=Mixtures.

As FIG. 17 shows, the invention compositions have a higher enzymatic activity than their equivalent solutions of only DNAse. For example, M0 and M13 with DNAse concentrations of 0.97 μg/mL showed halos of 13-15 mm while DNAse concentrations of 0.97 μg/mL alone (C2), showed halos of 8-10 mm. In addition, M15 and M16 with DNAse concentrations of 3.90 μg/mL showed halos of 17-20 mm while DNAse concentrations of 3.90 μg/mL alone (C4) showed halos of 13-15 mm. This demonstrates an amplified DNAse activity for Dornase alfa in the invention compositions.

Conclusion

The components of the compositions improve the DNAse activity of Dornase alfa and allows to extend the enzymatic activity in time.

Example 30

Angiogenic Capacity of the Composition

Angiogenesis is a complex biological process involving the generation of new blood vessels from the pre-existing vasculature. The process involves the cooperation of several different cell types, and in particular involves proliferation, survival, and tissue invasion by activated endothelial cells. Most investigations of angiogenesis include at least one in vivo study. The Chicken Chorioallantoic Membrane Assay (CAM) is suitable for a variety of applications. In this assay, the angiogenic properties of different concentrations of ethosuximide and lactic acid and the mixtures were tested.

Materials and Methods

Eggs commercial lines with a weight between 30-90 g were used. By using an ovoscope the viability of the chorioallantoic membrane was determined to select only fertilized and viable eggs.

Procedure: Prior to placing the eggs in the incubator, they were disinfected with povidone iodine and on days 6 to 9 of incubation the embryonated eggs were observed in the ovoscope to determine viability and control age. After that, the air chamber was identified, and the eggshell was carefully broken and trimmed facilitating the exposure of the internal testaceous membrane. The membrane was moistened with 2 ml of NaCl (0.9%) at 37° C. Saline solution was subsequently dumped and the testaceous membrane was carefully removed with a forceps in order to access the underlying chorioallantoic membrane. Eggs whose chorioallantoic membrane were damaged (presence of hemorrhage or any other injury) were discarded.

Then, 300 μl of the following solutions were slowly placed onto the chorioallantoic membrane: Ethosuximide 3.0 mg/mL; Ethosuximide 0.5 mg/mL; M0; M13; M15; LAPS; Negative control (PBS). Each solution was evaluated by triplicade.

Ethosuximide solutions and LAPS were obtained as indicated in example 1. While the compositions of the inventions were elaborated according to examples 18 to 21.

The eggs were covered with a transparent film and photographs were taken 5 minutes, 24, 48 and 72 hours after application.

Angiogenesis tests: Digital images analysis was made by using the software Image J plus. The length of vascularization (cm) per CAM area (cm$^2$) was evaluated before solution addition (basal) and after 24 and 48 hours. Then, the percentage of increase of vascularization was calculated.

Results

Figure 18:
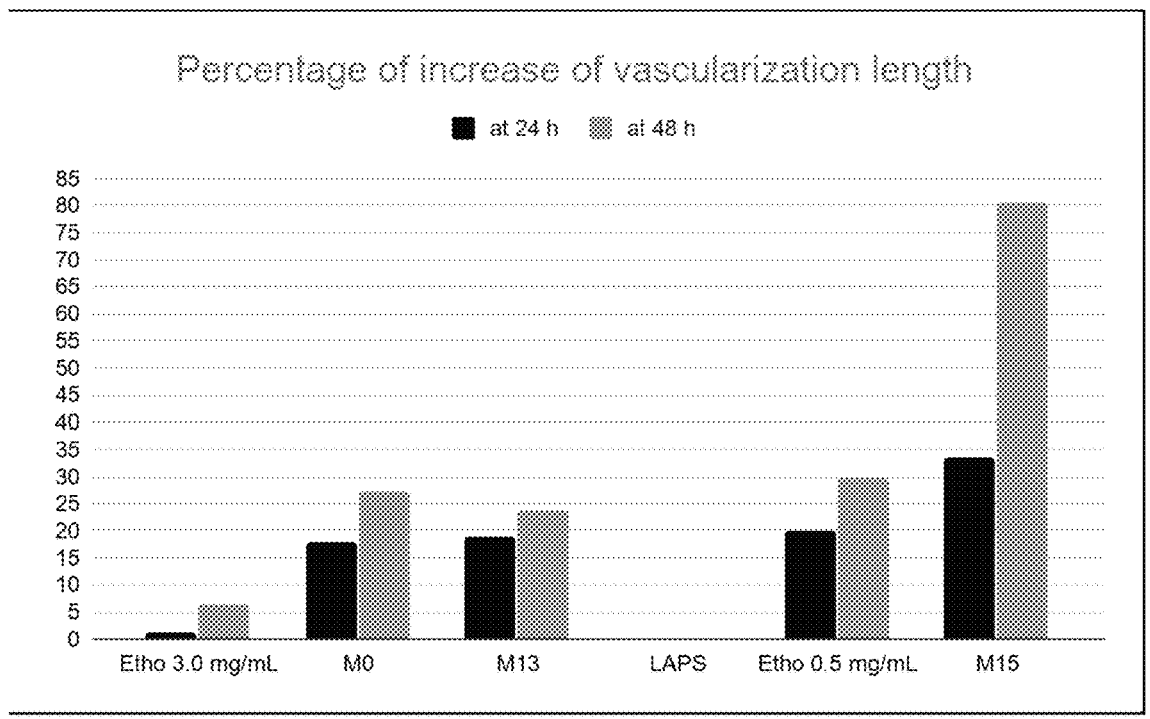
FIG. 18: Percentage of increase of vascularization in chicken chorioallantoic membrane. Etho=Ethosuximide; LAPS=*Lactobacillus plantarum* supernatant; M=mixtures.

The FIG. 18 shows the kinetics of vascularization in presence of LAPS and different solutions of ethosuximide, M0, M13 and M15. As it can be seen, LAPS did not show an angiogenic effect. Ethosuximide showed angiogenic properties although it was better at 0.5 mg/mL than 3.0 mg/mL. Mixtures M0, M13 and M15 showed an increased angiogenic effect compared to solutions with the same concentrations of ethosuximide.

Conclusion

The compositions of present invention surprisingly amplify the angiogenic power of ethosuximide.

Example 31

Regulation of Vascular Endothelial Growth Factor (VEGF) Expression With Ethosuximide Material and Methods Cell lines were grown and maintained following the protocols of the American Type Culture Collection (ATCC, Rockville, MD, USA), using Minimum Essential Medium (MEM), Fetal Bovine Serum (FBS), L-glutamine.

To evaluate the expression of the VEGF genes, the following cell lines were used:
  a. Murine macrophage cell line J774 (ATCC), stimulated with 25 ng/mL of lipopolysaccharides (LPS) from *E. coli* (L-8274, Sigma).
  b. Adult human skin keratinocytes cell line HaCaT (ATCC).

Cells were plated for 24 hours with Ethosuximide at different concentrations to evaluate their effect on gene expression.

Monolayers of the J774 Macrophage cell lines and HaCaT Keratinocytes were used, until confluent cells were obtained, which were stimulated with Ethosuximide at 0.5 and 3.0 mg/mL as indicated in example 1, in 12-well plates, at a final volume of 300 μL/well. For the J774 macrophage line, all treatments were supplemented with LPS (25 ng/mL), using MEM 1× with LPS (25 ng/mL) as control (Control+LPS). HaCaT keratinocytes were treated with the concentrations of ethosuximide in MEM with 10% FBS, using 1× MEM as a control.

The plates were incubated at 37° C. in a humid atmosphere with 5% $CO_2$ for 24 hours. Three replicate plates for each cell line for each experiment was done.

Levels of VEGF and GAPDH mRNA were measured in triplicate for each sample using the StepOnePlus Real-Time PCR Systems (Applied Biosystems) and the Power Up SYBR Green Master Mix (ROCHE) kit. The primer sequences for VEGF and GAPDH were: 5'-ACCTCCAC-CATGCCAAGT-3' (sense) and 5'-TTGGTCTGCATTCA-CATCTG-3' (antisense) for VEGF and 5'-CGAC-CACTTTGTCAAGCTCA-3' (sense) and 5'-CCCTGTTGCTGTAGCCAAAT-3' (antisense) for GAPDH. Mean values for VEGF were normalized to mean GAPDH values for each sample. Group means were determined and normalized to the MEM group for each experiment.

Results and Discussion

Figure 19:
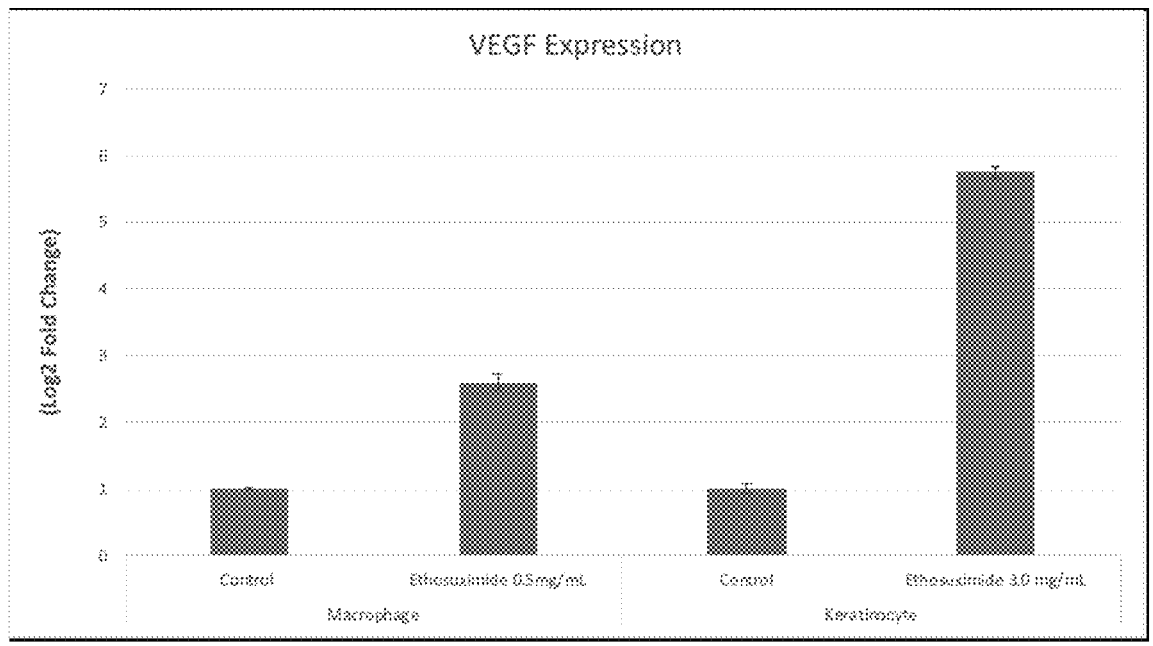
FIG. 19 shows the effects of Ethosuximide on VEGF levels normalized to GAPDH levels in Macrophages J774 and in Keratinocytes HaCaT, treated for 24 hours. Gene expression changes in log 2 scale. The Y axis is the Log-2-fold change in gene expression in each ethosuximide treatment relative to the control group. GAPDH served as a housekeeping gene to correct for cDNA input.

As a result, VEGF expression level was induced in both the Macrophage and Keratinocyte cells. The level of induction of VEGF expression occurs with Ethosuximide 0.5 mg/mL in Macrophages (FIG. 19) and with 3.0 mg/mL in Keratinocytes (FIG. 19).

During the proliferation phase of the normal healing process, angiogenesis occurs allowing the restoration of new blood vessels in the injured area under the regulation of angiogenic growth factors, such as VEGF (Vascular Endothelial Growth Factor) (43, 44). In chronic wounds, VEGF tends to show decreased or absent levels (45), and this is a probable cause of insufficient vascularization of the wound due to low activity (46). VEGF stimulates the uptake of apoptotic cells by macrophages through VEGFR-1 (46, 47). If this occurs during healing, the increased expression of VEGF in macrophages aids in the resolution of inflammation (46) and favors the passage towards the proliferative phase of healing.

Keratinocytes are also one of the main sources of VEGF during wound healing (46, 48). VEGF produced by epidermal keratinocytes works by regulating endothelial cells in blood vessels within the underlying dermis (46). Therefore, increased expression of VEGF in keratinocytes stimulates angiogenesis.

Conclusion: There is an increase in the expression of VEGF in macrophages and keratinocytes caused by ethosuximide.

Example 32

Wound Healing Effect of the Compositions (49)

Animals: 42 male rats of the Wistar/Cmedc strain, 8-10 weeks old, divided into 7 experimental groups of 6 animals each (Groups A, B, C, D, E, F and G) were used.

Excisional wound model (50): The surgery began by anesthetizing the animals and preparing the surgical area. To do this, the shaved back skin was washed and disinfected with Povidone Iodine and 70° Ethanol solutions. Subsequently, using a sterile 5 mm diameter biopsy punch, two wounds were made on the dorsal thorax (wound 1, corresponding to the left side and wound 2, to the right side of the animal), incising the skin and the fleshy panicle. After that, adhesive cyanoacrylate (Tegaderm™ 3M) was placed on each silicone ring and adhered to the skin, respecting the inside of the ring with the incision. When the adhesive fixed the skin and the silicone rings, five simple stitches were made to the skin, perforating the silicone ring in its external portion to secure the position using polypropylene sutures. After the surgery and with the animal recovered, an Elizabethan collar was placed in order to prevent the animals from removing the silicone rings.

Evaluation of bacterial colonization in the wound bed: In order to estimate the total unintentional bacterial load, in the wound 1 a swab of one animal from each experimental group was performed. The sample obtained was placed in a tube containing 10 ml of sterile 1× PBS and the total bacterial load was determined by serial dilutions and plating on agar for plate count (APC). After 24 h of incubation at 37° C., the CFU/wound were calculated.

Infection with Staphylococcus aureus ATCC 29213 to imitate the conditions of a chronic wound: Both wounds were inoculated topically in the animals of all the experimental groups. The inoculum was 10 µl of a bacterial suspension of S. aureus ATCC 29213, adjusted to McFarland's 0.5 scale in sterile 1× PBS (equivalent to $1.5 \times 10^8$ CFU/ml). Consequently, the final bacterial concentration obtained in each wound was $1.5 \times 10^6$ total CFU.

Treatment: Both wounds of all animals in each group were topically treated with the following hydroxyethylcellulose gelled compositions: Group A (M0), Group B (M13), Group C (M15), Group D (M16), Group E (LAPS), Group F (Mixing solvent) and Group G (Control without treatment). The first administration was made at 48 h post infection and then a daily application was made until the end of the trial. Before the application of the corresponding test substance, the wounds of the animals were cleaned using a swab and sterile physiological solution. Until day 7, 20 µl of each test substance composition was administered to each wound, reducing the dose to 10 µl from day 8.

The compositions of the invention (M0, M13, M15 and M16) were elaborated according to examples 22 to 25.

Observation and monitoring of the animals: The clinical signs, behavior and changes in the weight of the animals were evaluated daily. In addition, every 3 to 5 days the wounds were photographed using the Olympus Stylus SZ-15 digital camera and their areas were quantified using the Image ProPlus 6.0 program.

Necropsies: Animals 1, 3 and 5 of all experimental groups were sacrificed when the wound of the untreated control group reached 40% healing (around day 6 after surgery). Animals 2, 4 and 6 of all experimental groups were sacrificed when the wound of the untreated control group reached approximately 80% healing (around day 10 post-surgery). At the end point, animals from the control group were euthanized.

Histopathology: in the skin samples of animals 2, 4 and 6 of each group, epithelialization and collagenogenesis were determined by digital analysis of histological images stained with Masson's trichrome.

Immunohistochemistry: An immunohistochemical technique was performed on histological sections to detect alpha smooth muscle actin (α-SMA). A monoclonal antibody (Mouse anti-α-SMA—Clone αsm-1 Novocastra, NCL-SMA) was used, performing antigenic recovery in microwaves using citrate buffer at pH 6 and revealing the reaction with a streptavidin peroxidase system.

Results

Figure 20:
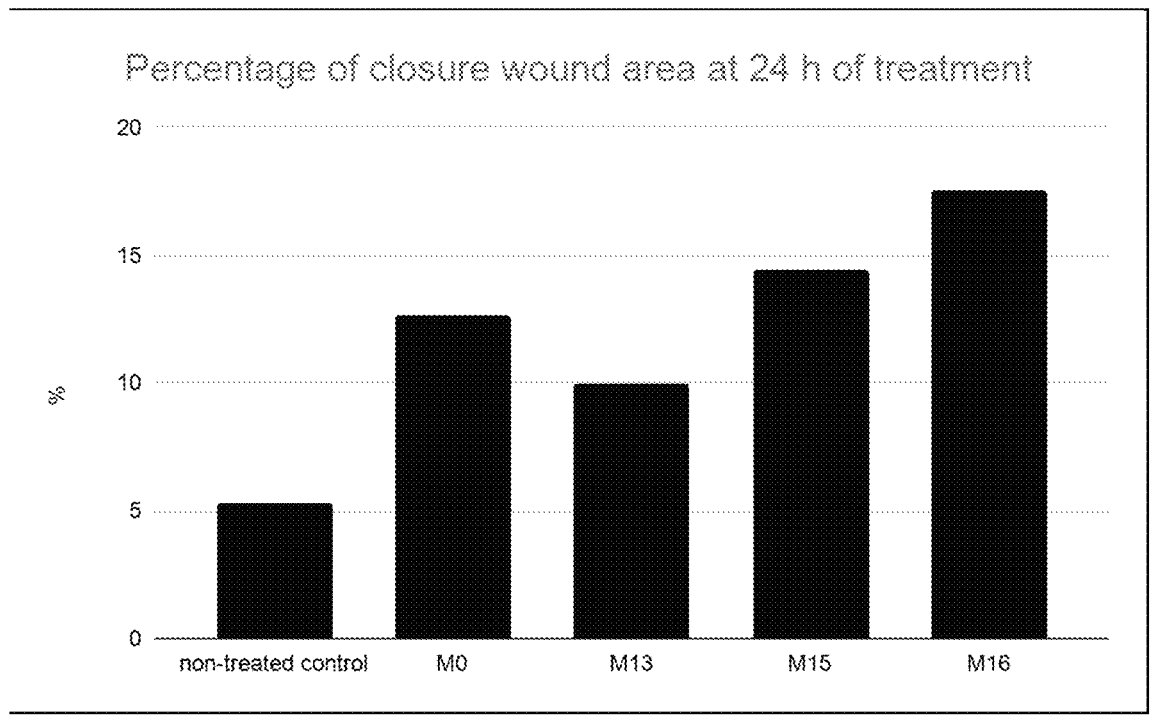
FIG. 20. Percentage of wound closure at 24 hours of the treatment applying in the different groups of treated animals.

The FIG. 20 shows the percentage of wound closure at 24 h of the treatment appling in the different groups of treated animals. The compositions (M0, M13, M15 and M16) were tested after 24 h post infection. The percentage of wound area closure was measured by analyzing photographs using the software Image ProPlus 6.0. Animals treated with M0 and M13 (with ethosuximide 3.00 mg/mL), M15 (with ethosuximide 0.5 mg/mL) and M16 (with ethosuximide 30.0 mg/mL) showed higher percentages of healing with respect to the non-treated control.

TABLE 2

Evaluation of collagenization using the Abramov score as histopathological classification. MS = Mixing solvent; LAPS = Lactobacillus plantarum Supernatant; M = Mixtures

| Group | Abramov scoring for collagenization | | | | | | | | |
|---|---|---|---|---|---|---|---|---|---|
| | A2a | A2b | A4a | A4b | A6a | A6b | Average | SD | Meaning |
| non-treated control | 1 | 1 | 1 | 2 | 1 | 1 | 1.17 | 0.41 | Scarce |
| MS | 2 | 1 | 1 | 2 | 1 | 1 | 1.33 | 0.52 | Scarce |
| LAPS | 1 | 2 | 2 | 1 | 2 | 1 | 1.5 | 0.55 | Scarce |
| M0 | 3 | 2 | 2 | 3 | 2 | 3 | 2.5 | 0.55 | Moderate |
| M13 | 3 | 3 | 3 | 3 | 2 | 2 | 2.67 | 0.52 | Moderate |
| M15 | 2 | 2 | 2 | 3 | 2 | 2 | 2.17 | 0.41 | Moderate |
| M16 | 3 | 3 | 3 | 3 | 3 | 3 | 3 | 0 | Abundant |

The presence of collagen was evaluated with Masson's trichrome staining in animals of all experimental groups (non-treated control, MS, LAPS, M0, M13, M15 and M16). The histopathological classification used to estimate collagenization is the Abramov scoring system, adapted from Nisbet et al., (2010) where the amount of collagen is classified as 0=absence of collagen, 1=scarce, 2=moderate and 3=abundant. Both wounds of each animal were studied with 5 high-magnification fields (400×) contemplating from the epidermis to the dermis. (Nisbet et al., 2010. Effect of three types of honey on cutaneous wound healing. Wounds 22:11;275-283).

Ajwee et al. (2012) Ajwee DM et al. (2012). Ethosuximide and phenobarbital promote wound healing via enhancing collagenization. Chemical Biology & Drug Design, 79(1), 137-142 applied ethosuximide (Etho) to excisional wounds in Albino rats model. They demonstrate that ethosuximide-containing ointments 10% w/w (80 mg/mL) in soft paraffin significantly promotes wound healing by enhancing collagenization. The inventors of this patent also applied ethosuximide combined with other components (M0, M13, M15 and M16) on Wistar rats in an excisional wound model infected with *S. aureus*. Composition of the invention allowed to obtain similar or better collagenization results but with minor quantities of ethosuximide (0.5 to 30 mg/mL) in infected wounds. Results from both assays can be seen in the following table. Data in the column Ajwee et al. were extracted from his paper and ethosuximide concentration of 10% w/w was transformed in 80 mg/mL by using soft paraffin density value.

TABLE 3

|  | Ajwee et al. | M15 | M0 | M13 | M16 |
|---|---|---|---|---|---|
| Animal | Rattus Norvegicus UJ-1 (Albino rats) | Rattus Norvegicus domestica (Wistar rats) | Rattus Norvegicus domestica (Wistar rats) | Rattus Norvegicus domestica (Wistar rats) | Rattus Norvegicus domestica (Wistar rats) |
| Wound type | Excisional | Excisional | Excisional | Excisional | Excisional |
| Wound thickness | Full | Full | Full | Full | Full |
| Infection | No | Yes | Yes | Yes | Yes |
| Pharmaceutical matrix | Paraffin ointment | HEC gel | HEC gel | HEC gel | HEC gel |
| [Ethosuximide] | 80 mg/mL | 0.5 mg/mL | 3.0 mg/mL | 3.0 mg/mL | 30 mg/mL |
| Collagenization | Yes | Yes | Yes | Yes | Yes |
| Staining for detection of collagen in tissue sections | Masson's trichrome | Masson's trichrome | Masson's trichrome | Masson's trichrome | Masson's trichrome |
| Day of measurement (post wounding) | 16 | 14 | 14 | 14 | 14 |
| Abramov scoring for collagenization | 2.42 (0.58) | 2.17 (0.41) | 2.50 (0.55) | 2.67 (0.52) | 3.00 (0.00) |

Figure 21:
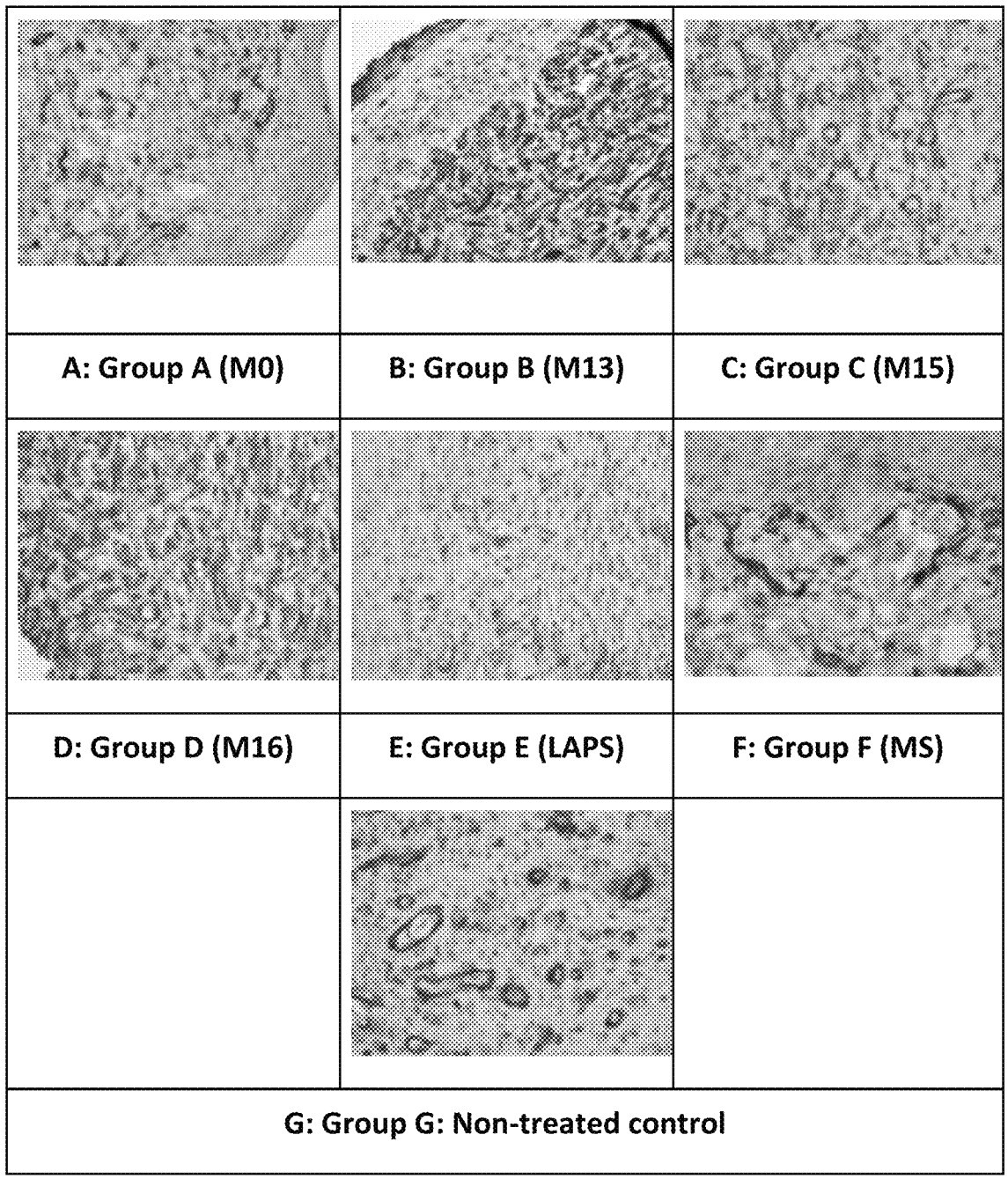
FIG. 21: Figure shows Immunohistochemical technique on histological sections from treated wounds to detect alpha smooth muscle actin (α-SMA) using a monoclonal antibody (Mouse anti-α-SMA—Clone αsm-1) and revealing the reaction with a streptavidin peroxidase system.

The alpha smooth muscle actin ($\alpha$-SMA) expression was studied as a specific marker of the muscle layers of blood vessels and myofibroblasts associated with the healing process. Myofibroblasts are specialized contractile fibroblasts that are critical in wound closure and tissue contracture. The expression of $\alpha$-SMA is seen in photographs (FIG. 21) as a brown coloration. Greater amount and intensity of brown color means greater $\alpha$-SMA expression. At 7 days post-surgery (the first end point of the trial), the non-treated control (FIG. 21G) and group treated with mixing solvent (MS) gel (FIG. 21F) only showed $\alpha$-SMA expression in blood vessels. LAPS slightly increased $\alpha$-SMA expression in myofibroblasts (FIG. 21E). On the other hand, compositions-treated wounds showed $\alpha$-SMA expression directly proportional to its component's concentrations. For example, M0 and M15 showed moderate expression (FIG. 21C), M13 showed high expression (FIG. 21B) and M16 showed very high expression (FIG. 21D).

Conclusion: Compositions of invention accelerate the healing process while stimulating collagen and alpha smooth muscle actin production, achieving a simultaneous bactericidal effect.

The invention claimed is:

1. A device for administering a pharmaceutical formulation kit, the pharmaceutical formulation kit comprising at least two of the following: about 1 to about 4 µg/ml recombinant human Dornase-alpha, about 0.5 to about 30 mg/ml of ethosuximide, and about 1 to about 9 mg/ml citric acid, wherein the device comprises at least two of the following:

a first container comprising a first composition, wherein the first composition is solid and comprises a gelling agent powder;
a second container comprising a second composition, wherein the second composition is solid and comprises the recombinant human Dornase-alpha; and
a third container comprising a third composition having a pH between 4.5 and 6.8,
wherein the third composition is an aqueous liquid comprising either the ethosuximide or the citric acid,
wherein the device comprises at least one of the following:

the first container and the second container are separated by a first collapsible membrane capable of keeping the first composition and the second composition isolated; and
the second container and the third container are separated by a second collapsible membrane capable of keeping the second composition and the third composition isolated.

2. The device of claim 1, wherein the device comprises the first container and the second container.

3. The device of claim 1, wherein the device comprises the third container and the second container.

4. The device of claim 3, wherein the third container comprises the ethosuximide.

5. The device of claim 3, wherein the third container comprises the citric acid.

6. The device of claim 5, wherein the third container comprises the ethosuximide and the citric acid.

7. The device of claim 1, wherein the device comprises the first, container, the second container, and the third container.

8. The device of claim 7, wherein the third container comprises the ethosuximide.

9. The device of claim 7, wherein the third container comprises the citric acid.

10. The device of claim 9, wherein the third container comprises the ethosuximide and the citric acid.

11. The device of claim 7, wherein the first container and the second container are separated by a first collapsible membrane capable of keeping the first composition and the second composition isolated; and the second container and the third container are separated by a second collapsible membrane capable of keeping the second composition and the third composition isolated.

12. The device of claim 11, wherein the third container comprises the ethosuximide.

13. The device of claim 11, wherein the third container comprises the citric acid.

14. The device of claim 13, wherein the third container comprises the ethosuximide and the citric acid.

* * * * *